(12) United States Patent
Kaeppler et al.

(10) Patent No.: US 11,178,832 B2
(45) Date of Patent: Nov. 23, 2021

(54) MUTATION OF THE ZMCIPK15 GENE TO INCREASE ROOT ANGLE AND TO ENHANCE ABIOTIC STRESS TOLERANCE IN MAIZE

(71) Applicant: Wisconsin Alumni Research Foundation, Madison, WI (US)

(72) Inventors: Shawn Michael Kaeppler, Oregon, WI (US); Hannah Marie Schneider, Cologne, MN (US); Jonathan Paul Lynch, Boalsburg, PA (US); Malcolm John Bennett, Tollerton (GB)

(73) Assignees: WISCONSIN ALUMNI RESEARCH FOUNDATION, Madison, WI (US); THE PENN STATE RESEARCH FOUNDATION, University Park, PA (US)

( * ) Notice: Subject to any disclaimer, the term of this patent is extended or adjusted under 35 U.S.C. 154(b) by 0 days.

(21) Appl. No.: 16/185,739

(22) Filed: Nov. 9, 2018

(65) Prior Publication Data

US 2019/0144879 A1 May 16, 2019

Related U.S. Application Data

(60) Provisional application No. 62/584,442, filed on Nov. 10, 2017.

(51) Int. Cl.
*A01H 1/06* (2006.01)
*C12N 15/82* (2006.01)
(Continued)

(52) U.S. Cl.
CPC .............. *A01H 1/06* (2013.01); *A01H 1/04* (2013.01); *A01H 5/10* (2013.01); *A01H 6/4684* (2018.05); *C12N 15/102* (2013.01); *C12N 15/1024* (2013.01); *C12N 15/8242* (2013.01); *C12N 15/8262* (2013.01); *C12N 15/8273* (2013.01); *C12Q 1/6827* (2013.01);
(Continued)

(58) Field of Classification Search
None
See application file for complete search history.

(56) References Cited

U.S. PATENT DOCUMENTS

| 2011/0167515 | A1* | 7/2011 | Zheng | ............... | C12N 9/1205 |
| | | | | | 800/278 |
| 2018/0077892 | A1 | 3/2018 | Kaeppler | | |
| 2019/0144879 | A1* | 5/2019 | Kaeppler | ............ | C12N 15/8242 |
| | | | | | 800/320.1 |

OTHER PUBLICATIONS

Xin et al. "Supplemental Data" Plant Cell (2013). 10.1105/tpc.113. 115592 downloaded from http://www.plantcell.org/content/plantcell/suppl/2013/09/13/tpc.113.115592.DC1/tpc115592_SupplementalData.pdf on Mar. 19, 2020; pp. 1-20 (Year: 2013).*

(Continued)

*Primary Examiner* — Cathy Kingdon Worley
(74) *Attorney, Agent, or Firm* — Quarles & Brady LLP

(57) ABSTRACT

The present invention relates to crop breeding. More particularly, the present invention relates to targeted modification of root angle to enhance abiotic stress tolerance in maize. In one aspect, the invention provides recombinant maize exhibiting increased root angle by decreasing the function of the maize ZMCIPK$_{15}$ gene. Methods of making the recombinant maize and various methods of plant selection and breeding are further provided.

16 Claims, 10 Drawing Sheets
(6 of 10 Drawing Sheet(s) Filed in Color)
Specification includes a Sequence Listing.

(51) Int. Cl.
  C12N 15/10    (2006.01)
  C12Q 1/6895   (2018.01)
  C12Q 1/6827   (2018.01)
  A01H 5/10     (2018.01)
  A01H 6/46     (2018.01)
  A01H 1/04     (2006.01)

(52) U.S. Cl.
  CPC ..... *C12Q 1/6895* (2013.01); *C12Q 2600/156* (2013.01); *C12Q 2600/158* (2013.01)

(56) References Cited

OTHER PUBLICATIONS

D. Gong et al. Constitutive activation and transgenic evaluation of the function of an *Arabidopsis* PKS Protein Kinase.(2002) JBC; vol. 277; pp. 42088-42096 (Year: 2002).*
GRMZM2G472643; Maize Genetics and Genomics Database: https://www.maizegdb.org/gene_center/gene/GRMZM2G472643; accessed on Mar. 19, 2020; pp. 1-4 (Year: 2020).*
Germplasm—definition (2020) downloaded from www.meriam-webster.com/dictionary/germplasm on Mar. 29, 2020; p. 1 (Year: 2020).*
He et al. Abiotic stresses: general defenses of land plants and chances for engineering multisress tolerance (Frontiers in Plant Science (2018); vol. 9; pp. 1-18 (Year: 2018).*
Hansey et al. Genetic diversity of a maize association population with restricted phenology. ((2011) Crop Science; vol. 51; pp. 704-715 (Year: 2011).*
UniformMu Transposon Resource (2011) downloaded from https://www.maizegdb.org/uniformmu; on Mar. 29, 2020; pp. 1-4 (Year: 2011).*
Till et al. Discovery of induced point mutations in maize genes by TILLING. (2004) BMC Plant Biology; vol. 4; pp. 1-8 (Year: 2004).*
Lynch, J. P. Root phenes for enhanced soil exploration and phosphorus acquisition: tools for future crops. Plant Physiol. 156, 1041-9 (2011).
Lynch, J. P. Steep, cheap and deep: an ideotype to optimize water and N acquisition by maize root systems. Ann. Bot. 112, 347-57 (2013).
Trachsel, S., et al., Maize root growth angles become steeper under low N conditions. F. Crop. Res. 140, 18-31 (2013).
Lynch, J. P. et al., New roots for agriculture: exploiting the root phenome. Philos. Trans. R. Soc. Ser. B 367, 1598-604 (2012).
Hammer, G. L. et al. Can changes in canopy and/or root system architecture explain historical maize yield trends in the U.S. corn belt? Crop Sci. 49, 299 (2009).
Tsuji W., et al. Development and distribution of root systems in two grain sorghum cultivars originated from Sudan under drought stress. Plant Prod. Sci. 8, 553-562 (2005).
Mace, E. S. et al. QTL for nodal root angle in sorghum (*Sorghum bicolor* L. Moench) co-locate with QTL for traits associated with drought adaptation. Theor. Appl. Genet. 124, 97-109 (2012).
Bonser, A., et al., Effect of phosphorus deficiency on growth angle of basal roots in Phaseolus vulgaris. New Phytol. 132, 281-8 (1996).
Oyanagi, A. Gravitropic response growth angle and vertical distribution of roots of wheat (*Triticum aestivum* L.). Plant Soil 165, 323-326 (1994).
Zhu, J., et al., Topsoil foraging and phosphorus acquisition efficiency in maize (*Zea mays*). Funct. Plant Biol. 32, 749 (2005).
Liao, H. et al. Effect of phosphorus availability on basal root shallowness in common bean. Plant Soil 232, 69-79 (2001).
Manschadi, A. M., et al., Genotypic variation in seedling root architectural traits and implications for drought adaptation in wheat (*Triticum aestivum* L.). Plant Soil 303, 115-129 (2008).
Shen, L., et al., Evaluation of near-isogenic lines of rice introgressed with QTLs for root depth through marker-aided selection. Theor. Appl. Genet. 103, 75-83 (2001).
Oyanagi, A., et al., The gravitropic response of roots and the shaping of the root system in cereal plants. Environ. Exp. Bot. 33, 141-158 (1993).
Uga, Y. et al. Control of root system architecture by Deeper Rooting 1 increases rice yield under drought conditions. Nat. Genet. 45, 1097-1102 (2013).
Zhu, J., et al., Detection of quantitative trait loci for seminal root traits in maize (*Zea mays* L.) seedlings grown under differential phosphorus levels. Theor. Appl. Genet. 113, 1-10 (2006).
Zhu, J., et al., Mapping of QTLs for lateral root branching and length in maize (*Zea mays* L.) under differential phosphorus supply. Theor. Appl. Genet. 111, 688-95 (2005).
Hund, A. et al. QTL controlling root and shoot traits of maize seedlings under cold stress. Theor. Appl. Genet. 109, 618-29 (2004).
Zhu, J., et al., From lab to field, new approaches to phenotyping root system architecture. Curr. Opin. Plant Biol. 14, 310-7 (2011).
Hochholdinger, F., et al., Cooperative action of SLR1 and SLR2 is required for lateral root-specific cell elongation in maize. Plant Physiol. 125, 1529-1539 (2001).
Hansey, C. N., et al., Genetic diversity of a maize association population with restricted phenology. Crop Sci. 51, 704 (2011).
Hirsch, C. N. et al. Insights into the maize pan-genome and pan-transcriptome. Plant Cell 26, 121-35 (2014).
Bayuelo-Jiménez, J. S. et al. Genotypic variation for root traits of maize (*Zea mays* L) from the Purhepecha Plateau under contrasting phosphorus availability. F. Crop. Res. 121, 350-362 (2011).
Nakamoto, T., et al., Elongation angle of nodal roots and its possible relation to spatial root distribution in maize and foxtail millet. Japanese J. Crop Sci. 60, 543-549 (1991).
Kato, Y., et al., Genotypic variation in root growth angle in rice (*Oryza sativa* L.) and its association with deep root development in upland fields with different water regimes. Plant Soil 287, 117-129 (2006).
Hargreaves, C. E., et al., Measuring root traits in barley (*Hordeum vulgare* ssp. *vulgare* and ssp. *spontaneum*) seedlings using gel chambers, soil sacs and X-ray microtomography. Plant Soil 316, 285-297 (2008).
Norton, G. J. et al., Mapping of quantitative trait loci for seminal root morphology and gravitropic response in rice. Euphytica 166, 229-237 (2009).
Liao, H. et al. Genetic mapping of basal root gravitropism and phosphorus acquisition efficiency in common bean. Funct. Plant Biol. 31, 959-970 (2004).
Omori, F. et al., QTL mapping of root angle in F2 populations from maize B73 × teosinte *Zea luxurians*. Plant Root 1, 57-65 (2007).
Guingo, E., et al., Genetic analysis of root traits in maize. Agronomie 18, 225-35 (1998).
Burton, A. L. et al. QTL mapping and phenotypic variation for root architectural traits in maize (*Zea mays* L). Theor. Appl. Genet. 2293-2311 (2014).
Uga, Y. et al. A major QTL controlling deep rooting on rice chromosome 4. Sci. Rep. 3, 3040 (2013).
Vidal, E. A., et al., Gene networks for nitrogen sensing, signaling, and response in *Arabidopsis thaliana*. Wiley Interdiscip. Rev. Syst. Biol. Med. 2, 683-93 (2010).
Stelpflug, S. C. et al. An expanded maize gene expression atlas based on RNA-sequencing and its use to explore root development. Plant Genome 314-362 (2015).
Kolukisaoglu, U., et al., Calcium sensors and their interacting protein kinases?: Genomics of the *Arabidopsis* and rice CBL-CIPK signaling networks. Genome Anal. 134, 43-58 (2014).
Sekhon, R. S. et al. Genome-wide atlas of transcription during maize development. Plant J. 66, 553-563 (2011).
Kumar, P., et al., Predicting the effects of coding non-synonymous variants on protein function using the SIFT algorithm. Nat. Protoc. 4, 1073-1081 (2009).
Jung, J. K. H., et al., Getting to the roots of it: Genetic and hormonal control of root architecture. Front. Plant Sci. 4, 186 (2013).
Wasson, A. P. et al. Traits and selection strategies to improve root systems and water uptake in water-limited wheat crops. J. Exp. Bot. 63, 3485-3498 (2012).
Tuberosa, R. et al. Searching for quantitative trait loci controlling root traits in maize?: a critical appraisal. Plant Soil 35-54 (2003).

(56) References Cited

OTHER PUBLICATIONS

Trachsel, S., et al., Shovelomics: high throughput phenotyping of maize (*Zea mays*L.) root architecture in the field. Plant Soil 341, 75-87 (2011).
Zhang, Z. et al. Mixed linear model approach adapted for genome-wide association studies. Nat. Genet. 42, 355-60 (2010).
Lipka, A. E. et al. GAPIT: genome association and prediction integrated tool. Bioinformatics 28, 2397-9 (2012).
Gao, X., et al., A multiple testing correction method for genetic association studies using correlated single nucleotide polymorphisms. Genet. Epidemiol. 32, 361-9 (2008).
York, L. M., et al., Intensive field phenotyping of maize (*Zea mays* L.) root crowns identifies phenes and phene integration associated with plant growth and nitrogen acquisition. J. Exp. Bot. 66, 5493-5505 (2015).
Postma, J. A, et al., The optimal lateral root branching density for maize depends on nitrogen and phosphorus availability. Plant Physiol. (2014).
Lynch, J. P., et al., SimRoot: Modellig and visualization of root systems. Plant Soil 188, 139-151 (1997).
Postma, J. A. et al., Root cortical aerenchyma enhances the growth of maize on soils with suboptimal availability of nitrogen, phosphorus, and potassium. Plant Physiol. 156, 1190-201 (2011).
Kamburova, Venera S., et al. "Genome editing in plants: an overview of tools and applications." International Journal of Agronomy 2017 (2017).
UniformMu Methods, https://www.maizegdb.org/uniformmu, Mar. 2011.

\* cited by examiner

FIG. 4

Genomic DNA sequence of gene model based on B73 RefGen_v3

>Zm00001d033316 Zm00001d033316 (SEQ ID NO:1)
ATGGCCAAGAGCAAGTCGTCCGCCAAGGCCGGCCCCCGCTCCTCGGCAAGTACGAGCTCGGCCACCTCCTCGGCCGG
GGCAACTTCGCCAAGGTATACCACGCGCGCTGTCTCGGCGGAGGCGACCCCGTGGCCGTGAAGGTGCTGGACAAGGCC
GGGTTGGCCGCCACGGGCATGGCGTCGCGTCTCCTGCGCGAGGTGTCCGCCATGCGCCGCCTGAGCCACCCCAACGTG
CTCCGCCTCCACGAGGTGCTGGCGACGCGCTCCAAGGTGTACCTCGTGATGGAGCTGGCCCCGGGCGGGGACCTCCTG
ACCCGGCTGGCGTCGCTGCCGTCGCGCAGGCTCCCCGAGCACGGCCGGCGCGTGTTCCTCCAGCTGGCGTCGGCG
CTCATCTACAGCCACGCGCGGGGTGTTCCACCGCGACGTGAAGCCGCAGAACGTGCTCTGGACGCCGAGGGCAAC
CTCAAGGTGTCCGACTTCGGCCTCGCGGCGCTCCCCGGACTCGGTCCGCGACGACGGGCGCCTGCACACGGCGTGCGGC
ACCCCGGCGTTCGCGGCGCCCGAGGTGCTCCGGCGCAGGGCCTACGACGGCGCCAAGGCGGACGCGTGGTCCTGCGGG
GTCATCCTCTTCGTCCTCCTCGCGGGCCACCTCCCCTTCGACGACGCCAACATCGCCGACATGTGCCGCAGGGCGCAC
CGCCGGGAGTACACGGTCCCGCGGTGGGTGTCGCAGCCGGCGCGCCGCCTCGTGGCGCGCCTGCTGGACCCGAACCCG
GCGACGCGCCTCGCCGTCGCGGAGCTCGCCGGCCACCCCTGGTTCAAGCGCTCGCTCAGCGTGGACTCCCAGCTCGGC
GGCCTCCTGGACGGCCAGGCGGAGCGCGAGCTGGCGTTCCAGGCCCCGCCGGCGTTGAACGCCTTCGACATCATCTCC
ATGTCCCCCGGGCTGGACCTGTCGGGCCTGTTCGGCGAGGGCAGGCGCCGCCGCGAGAAGCGGTTCATGACGACGGCG
TCCCCGGAGCGGGCGGTGGAGCGGCTCGCGCAGGCCGGCGCGAGGCTCGGCTACTTCATTGTGGGGAAGAAGGGGGCC
GAGCGCCTGCCGCTGGGCGTCCTGCCGGGCCTCGTGGCCATGTCGATGGAGATGTCGGAGGTGTCGCCGGAGCTGATG
CTGGTGGAGCTGAGGCTGGAGGGCGGCCACGGCGACGAGGACGAGGCGTTCGGGTGGGAGGAGCTCCGGGTTGAGCTG
GGGGACGTGGTAACAGCATGGCACGTGAGTGAAGAAGGTTAA

Sequence from Zm-B73-REFERENCE-GRAMENE-4.0 including gene model at coordinates
258845263..258848552 and 5.0 kb upstream and downstream of the gene model >Chr1:258840263..258853552 (SEQ ID NO:2)
CACTTTCGGACTTGTCCATTGAAATTGATCCCATAAACCCTAGTTTACTAATTCAAATGA
AATATGTGTGTGTATGTGTGAAGGATCTCTATGCGGTACGCAACTGGTTTTGTATATATA
TGGCAGCACTTACATGTTTAAATACTTGCAATATGTGAATATCATAGAAGAACAGCTAAA
GTAAAATATGAGCGCACAGTAAGATTTTCTAGTATACACAAATTAAGTAACTTTATCAGC
TGTACTTTTTAAGTTTATATTTCTACTGACGATTAAACTATATAAAAGGCCAGTACAAAA
ATTTATAGATGTTCATGTTCTTAGCAACCACGCACGATTTTGGCTTTTTCTTTTAACTT
CTGATTTTGAAGGTCAGAATTCTATATGTGCATATATTCGCGTACCAATACTTCATGTGC
ACCGGTTATTATCTCTAATACCTTAGCATATTGCTGGTTCATTAGTATAAGCAAACTAGC
TAGACTGGATCTGCTGTGCACACTACTATAACAGTTCAGACTTTTATAGATAGGCACTAC
TATTCCTCTTCCATGAGGAGACTACTCGATCATATAATAATCTACGCTCAGTTAAGATA
AGGCCCTGTTTGTTTCAACTTATAGATTATATAATCTATATTATAATTTAGATTATATAA
TCTGGATTATTTGCTCTGGATTAAATAAGCTAGGTGCTACTGTTTGTTAGCTCAGATTAT
TTGGACTCGGCTTATTATTCATATGCATACAAATACAATAATACCCTTGATTGTTTTAAT
TGTCTGGTGGGTGAGAACGCTTATAGATAGGTGGATGACAATTGGAAGTAATTTTAATCA
ACTTGCCATGGGTAGTGGGTCTTTCATAAAAAATAAGCTGAAATAAGCACCCTTTGATGA
GCTTATAGGATTATCATAATCTCAAGTGCTAGATTATATAATCTTATCAGATAAGTTGTT
TGTTTGTTTCCTCACTAGCTTATTTACATTGGATTATATAATCTATATAGATTATAATCT
CAAACAAACATGGCCTAAGTTGGCATAAATCGATTATCTACTAATAGGCAAAGTTTTTCC
TGGTGCAGCAGACCGACTGTGCATGCATGTTTTGAAACTAACGCAAACACGTACAGTCGT
ACACTGGTTTCGGTCGAACCGAAACGAGAGACTTGCTTTTTTTAGTTGATTTACTACTCTT
GGTCCAAAAGGAATATGTGCGTTCAACTCTTTGAATTGATCGAAACGAATTAATTAGTAT
CCCCTAACTATGAAAATAATATGACCGAGATAATTTTGGTTGAAATGCAAGATGCCATAC
ACATATGCCTGTGAAATGCTAGCTGGAGTTCAAAAGCAGATTGCGACGCGCAAAAAAGG
ACACACAACAAGAGGATGATTTACTTCACTTTGAAGTGAAGTCTCTCAAAGCGGAGAGAA
GAAGATATACATGCACACTAGCCAACGCAGCATTGATCCATATAGATATATAGTAGCGCT
CGAATCGAACTAGAGAATAGCGATGTTGAAACTAGACCTGGCAAAAATATCTATCGTCTC
CCACATGCATCGTCAATTAATTTTAGGTGGTGTTTGATTGCACTAGAACTAATAGTTAAT
TAATAGTTAATGATTACATTAAAAACGTCCTAGCTAATGGTTCAACTATTAACTATTTTT
TTTTGTAAATTAGTTAATAATAAGCTAGTTATTTGTTAGCTAACTAATTTCATTAGTAAT
TTTTAGTCGACTAATAATTCAAAATGAGGTGGTGCATCACTCGGTTCATTTATCAAGTTTG
GTGGAATGATCTCATTTCTCATATTAGTATTAACCAACTAAGAGCAATGAGGTGGACTTA
TTTCATTCCACAAACCAAACGAAAAAAGTGAGAAGTGAGAAGATGATATGGACTAGCTCG
TTCCTTAAAACAAACACCCTATAAATATCGAATTCATCGTTTAGATTAATGTTTTTTTAA
ACTATATATATAAATACTCCTGTGGAGAGCATGGGTTCATTTGTTTGCAATACATGCATT

FIG. 4 CONTINUED

ATGCATAGTGGGGTTAGATGGGCGAATGCGATTCGATCGTTTGATTAGTCTCAGGCTCTC
TCATATGTAGCAGCTAGTGCGAGATCTTCTGGCTGTGTTACTTTGCATGTCACATGTTCA
TGGTTCAGTTCGCCCTTTCCGGTATCCCAAAGGTTACTTGCACTGCGCTAGCTGCTGTTG
TTTAAGACTTTGCATGAAACAAGTGCATCCTTCGTTTTAGAAAAGAAAAACTAATTAAAA
TAAAAGGCTGTATCTCCAGTATGATCGGCACAGGTGAAAAGCTTCGGCTTTCAGCGCGTA
TTTTGGACGGACGTGTAGATTTGCATCTCCTTGACGAGAAGCTTGCACTAGCCCAAAGCT
TGCACTTGCGCATGTTCGAGAGAGAAAAAAAATCCGATCCGTGTATAGATCTCTTTCTGG
AGGAGGTGTGTCGGTTGGAATAATATATATATCTTCTACAAATAAAAGGCCTCTCGCACA
TTATTTTCTGTTTACACAAGTTTGTAAAAGGTTCCTCATGAACATTTATACATGCTTAAA
CAAGCTAATAAACACGGTGTTTTTCTCCCCCTTTTTTCCCCAGGATTCTTTGGAGATAG
GGGCCTTTGGAGATTAGAAAAAACATCTAGAGCGTCGTCGTCGGCACCGATGCAATGAGG
GTCTCTGCTTCCTCTTTGATTCATACGCAGAAAGTGTTTCATGCTCCTCTGTATATGTTG
AAAGTATTGTTGATAAGGCTCATTCTTAATGCGGTGCTCTTTTTTTTTAAAAAAAGA
ATAGATTAGATCATGTAAAATTTTTGTATAGAAAATAATATTTTATGGTTGAGTGGGGTA
TATGTAGATAATTTAGGGGTAACCACTGCGGGAAAACAAAAGTAGGGGGTAGAATCTGG
ACAGGCTGGGATCTAGGAATCTCCCGTCCCCGCTCATGCATCCAATCAGTGAAAAGCGG
CATGCATTGTACCGCACGTGTCTGTGCATACAACCAATCAGGGGTTTGCACGCATGCGGA
GGACATGACGCGGGTAGCAGGGAAACCAATCATGCGAAATAGGTTTTTGCAGGTGCATG
TGCGTATATAACCACCCGCGCGCAGGAGTAGGGATGCGTATAATAGATAGAATGATGAAG
ATATATCTGCGTAGGCTCGGTGATGTTTGTACGATGGATGAATTGAAGGCGGCATTTCCC
ACTTGCCTGCGCTACGTACCGACGGTGTGCTGCGGGCGACTGGCGAGAAGGAAGGGGAC
AGACACGCACGGCATGTCGGCATCCAGCTGCTGGTGCGCACCCAACGCAGGCAACCGACG
GAGGAAAAACGAAAAAGGAAACCAGCCAGGCTCGCGACGCTGCTGCTGCTGGGCGGG
CGCTCTGCTAGCCGTTGGTTGGCACGACAGATAATGATAGATGGATCCAATCCAACGCAC
CACCCCGTCCGTGTCACGACGGCGGATCGGAAGCCAGAAAGCAAGGGGCTGCTGCTGGCT
CTGGCTGGTCCATCAGTCATCACGTATACGCGTATCGACCAGCCGCCTATGCGCGCGCAG
GCAGTGCAAGAATGAACGAACGTTCCCAAGTGCAGGTGACCCGTGACCGTAGGCGTGAAC
CACCGGTCTAACTAGTCAAGTACTAGCTACCAGGTAGTTTGCCATATGTATCTGAGATAG
TGTATGGCGCCCGAGGCGAGACGTTTTATCTACGTACTGTACTCCACACTTGGCGCTAT
CCTGGATGTTCCTGTTGCCGCCGGGGACGGGAACAACACCGTAGCGCCTAGCGCGGGTGC
GGGCGCGGGTGGTGACATCTGATGTACGCCACCGGGCTCCGGAGCGCGACGGCCAGGCAG
CCCCGGCGCCACACGCGGCGCGCTAGCTAGATTTTCTTTCCCCGAAAAAGCTGGACGGGG
ACCTCGCCCTCGCCGCGCTGGTTCCGTTCCGTTCCGCCCCGCGGATATTTTCGTGGAGC
CTCCCCACCCCGCGGCGACCCCAGCGGGCAGCGGCTCCTTTCCGCGTCCGCCGCCGCACC
CGCGTCTCGGTCTACGGTCTCTCGTCACGTCTCGCTCTCGCACCTCACCTGCGCACGGCG
CCACCACAGGATGCTCTGTCTCCCTCTCTCCCACTCCCAGCTTTTGTGAGGCCAGAGCAA
CGTCCAGGAACCTCTGGTGCGTGGGAGAATCGGACGCCGCGTCCTGCCTCTCCCAAGCTC
CAAAGGGCGGGCACTTGACACGTACTGGCAGTAGGCTCTCTACCCGATCATCAGAAACGC
CAGCAAACAGATCAGCTCCCCCGCGCCGCGCTGCGCTGGAGAGCTGGAGGAGGAGAGCAA
GAGAAAAAAAAAATCTCAGGTTCCGCCCGCCGTGGCAACTGGCAACCGAGTTCCTTGTCC
TTTTTCCGAGTTCGTGTTGAACTCAATTCTCAGAGCCTGGTTCACACGCTTGAAGATAGT
ATCTTACACAATTCTACCTTGCAAAAATGTTTAAGGGTTAGTTTGGGACATAATTTTCT
TAAGATTTGTTTATTTTTCCAAAAGAAATTAGCTCATTTTTCTGGGTAAAATAGAAAATT
TCTTAAAAAATGGAGTTCACAAATTAGCCCTAAATATTCAGGGATTTCCACATCTGTTA
CATAACTCCCATAGCATCGCTACAAATTTCAGAGGAAAAAGGAGACCATGTCCATGTAT
CTTCTCCAAAAACAACCATTAAAGTTCAGAGGAAAAAGGAGGAGATTTTTTTTTCTTT
TTTGGCGAGGAGGGGGAACAAAAGAAATATCGTCTTGTGAGCTGCTGGCCTTGGTATT
AAAAATCTGGAGACCATGAATATTGGCCTTCTGTGCAAGTGGTGGTGGAAAATATCCAAA
ACTCTGACTCCCCATCCGGGAAAATTGACTAAGGTGAGGGATTATTTTTTTAGATAA
TGTAGGTAAGGAATTATTATCTTAAGGGCATGATCATTGTTACTAAATCCGGATACAAAA
CTGCCTTCTCGACTGATAATTGGCTAGATAGGGAGCCCATGAACATTACTCACCCAGATC
TTTATGAAATATGTGATGAAAAGGATATCTCGGTTAAGAATGCCAAAGAAGAAAAAAAA
CTAGCAGCTAAAATTCACAATGTTGATGAATTATGACTTATGAGAATCAATTAACTGGGA
TAACCTCTTTACGGAGTTCAAAGATACTTCTCAACCTTTTCATGTCTTGGTTCAAATATA
AACCTTCCAAATACAATAAGGCCTTGTTTGTTTACTCTATAGACTATGTAATCCAGTTTA
ATTAAGTTAAAAGACAAACAAACAACATATATTATTAGGTGGATTATACAATCTATAGCT
AGATTATGATAATTCATAAGCAGATCATTATATAATTCATAAGCTAGATTATATATTCGG
GAAGAAAACAAGCAGGGTTTAAGAGTGTGTTTGTTTGGGATTATAATCTGCCTAGATTAT
ATAATCTAATAAACTATAGTTCAAAAAAATTTGGGTTATAATAGCATATAGCCCGTGCTA
ACGTCACGATCTCGCGAACGAGGGTAAATATGTTCACGGCGGCGGCGCAAGTGAGGGAAG
GGAGCAGCACTGGACAAGGACGCAGGATTATAATTTGTAGTGATAATCTAGCTAGATTAT
AATCTCAAACAAACATTCCTGATTCTTGAATGAAAATGTAGCGGTAGTGCCAGTAGGGTC
ATGGATCTAAATGACGTGATCACTGTGATCATATCTTGCAGCTATAAATACAAAATGCCA
ATGACAGGAACCAGAGGAGGCACGAGAGCGCCATACATACACAAACAGCGTACAAGACTC

FIG. 4 CONTINUED

```
AACCACTCCCTCCTTGTTTGTTTATATACCTTGGCACCACCAAGGCAGCACCCTGTAAAC
TAACTACCAAAGCCGAAGAAGGCGGCTTGCCCTGCCCGTCGCCTTGGTGCCGCGCGCGCC
ATGGCCAAGAGCAAGTCGTCCGCCAAGGCCGGCCCCCGCTCCTCGGCAAGTACGAGCTC
GGCCACCTCCTCGGCCGGGGCAACTTCGCCAAGGTATACCACGCGCGCTGTCTCGGCGGA
GGCGACCCCGTGGCCGTGAAGGTGCTGGACAAGGCCGGGTTGGCCGCCACGGGCATGGCG
TCGCGTCTCCTGCGCGAGGTGTCCGCCATGCGCCGCCTGAGCCACCCCAACGTGCTCCGC
CTCCACGAGGTGCTGGCGACGCGCTCCAAGGTGTACCTCGTGATGGAGCTGGCCCCGGGC
GGGGACCTCCTGACCCGGCTGGCGTCGCTGCCGTCGCGCAGGCTCCCCGAGCACGCGGCG
CGGCGCGTGTTCCTCCAGCTGGCGTCGGCGCTCATCTACAGCCACGCGCGCGGGGTGTTC
CACCGCGACGTGAAGCCGCAGAACGTGCTGCTGGACGCCGAGGGCAACCTCAAGGTGTCC
GACTTCGGCCTCGCGGCGCTCCCGGACTCGGTTCCGCGACGACGGGCGCCTGCACACGGCG
TGCGGCACCCCGGCGTTCGCGGCGCCCGAGGTGCTCCGGCGCAGGGCCTACGACGGCGCC
AAGGCGGACGCGTGGTCCTGCGGGTCATCCTCTTCGTCCTCCTCGCGGGCCACCTCCCC
TTCGACGACGCCAACATCGCCGACATGTGCCGCAGGGCGCACCGCCGGGAGTACACGGTC
CCGCGGTGGGTGTCGCAGCCGGCGCGCCGCCTCGTGGCGCGCCTGCTGGACCCGAACCCG
GCGACGCGCCTCGCCGTCGCGGAGCTCGCCGGCCACCCCTGGTTCAAGCGCTCGCTCAGC
GTGGACTCCCAGCTCGGCGGCCTCCTGGACGGCCAGGCGGAGCGCGAGCTGGCGTTCCAG
GCCCCGCCGGCGTTGAACGCCTTCGACATCATCTCCATGTCCCCCGGGCTGGACCTGTCG
GGCCTGTTCGGCGAGGGCAGGCGCCGCCGCGAGAAGCGGTTCATGACGACGGCGTCCCCG
GAGCGGGCGGTGGAGCGGCTCGCGCAGGCCGGCGCGAGGCTCGGCTACTTCATTGTGGGG
AAGAAGGGGGCCGAGCGCCTGCCGCTGGGCGTCCTGCCGGGCCTCGTGGCCATGTCGATG
GAGATGTCGGAGGTGTCGCCGGAGCTGATGCTGGTGGAGCTGAGGCTGGAGGGCGGCCAC
GGCGACGAGGACGAGGCGTTCGGGTGGGAGGAGCTCCGGGTTGAGCTGGGGGACGTGGTA
ACAGCATGGCACGTGAGTGAAGAAGGTTAAAAATTCGCAAGAGGAAATGCGAGAACGATT
TCGCAGGTGTATCAGTGTAGCATGTATAGCCGTATAGCAAGTGCGCATCTCATCTCGTGT
ACGTGAAATTAGTTGGTTAGGACGAACAGCAGCGTGTGATGTTGGGGATTAACTAGACTG
GTAGTTTCAATCAAATGTGTGATGTTTGGGATTATTTGTCAAATTAGTACGTATACTAAA
GACCTTACTAGGTACCTCGCGTGATTGTTGTTCAAGTGTACTAGCTACCAAGCTAGTGAC
AAGAATGTTGCAAGGATATACCAGAGGAAACTGTTTCAAAGAATGAGCTTAACTTGAACT
GATTGCAGCATTAAAACAGTTTCCTTGTCCAGTCGTCGAATGGAGCTCTCCAAACTTGAC
TGCACATTCCCATTGTTGCATGGACTCGTGGTTCTTCCTTCCCTGACAGCGGCTGCCAAAC
CGCCGCAGCGACGCCGTCCGAATGATGCAGCTAGCTGCGTGCCTGCACCCACCCAGATCC
AGCAAAATACATGCTGCCTCCGAGATCCTCCCATGAGGGCGTGGCAAATTCTTTCTTGTC
TATGTGCTTTGGGCCGGGGTGGGGGTGGCAAATGCATCTATCTATATGCGGTCAACCGTT
TAAGTCCATCCAATTAAGGTTCAGGTTCAAGGTGCTGTCCAACTCGATGTCACCTGCTCC
TTCATCAGGTTGATGAAGAATATATATAATACCATCCCAATTATGGTTGGCGAATTGAAG
AAGAACCATAGCGCAAAAGGTTGACAGGCATGTCTACTAGCATTACAGCGAAGATTCATG
GTGCAAGTCGTAGTCGGTTTACAGGCAACGCCCTCCAGCAGCAGGGACTAAAATGGCCAT
GGCGTGCGTGATCAGATGGATGGCGAACGGAGAAATTTAAAACGGAGACCACATCATCTT
CAGTGACTTGTAGGCTCCGGGCTCTGGCAGCACCGAGCTCATGGCGGACGAGGATGAACA
TGTGTCAATGGAACTCCGTGGAAACCACACACCAGTCATCTTGCTGTCCATTAAACACGT
CAAATGTCGACCCGCACAAGGCACGTACGCGCGCGGACCACATCTCTCGTTCATCAAGCT
AGCAGCAGTTCAAGTCAACTTTGCCGAATGCATGCTAACGGCTGAACTGTTGATTCAAGT
AGCAGTATCGGCAGGCAGCTGCAAGCTGTGGCCTCCCTGCTACATATACTAGGTAGCTAG
TGGTGGTCTGGTGGATGCGGTGCTAGATGGGGACGAATGAAAGCGAGAATCAGTAAGACC
CCGGCCGGAGGAGAAAAAGGAGTGATGCTCTTGGCTGGCATGGACGTCGCCGATCAGGGG
AAACGAACAAAGCGAGATCGATCAGCCCGGCAGGGGTATGGCAAGATGACAATGCAAGCA
GCTTGTATTGTATCCTTGTGCCGGATAATTTAATTAAGCATACAGTTTTCTCCCTTCTGA
CGTACGGCCTCATCCAGCCTGCGAAGTGGTGAAAGTGAACTGAGCGTTACAGCAGAATAC
CAGATGCGACTAGCTGAAACGCCGGGTTTTGGCCATAGATCCAAGAGAAAGAAGCTCAAG
TGGAACCACAAGCGCAAGAAACTAAGAATATATTTTGGTCAGGTCATCCGTTTCACAAGA
AAACTGAGTTTATTTTCAATTCAGATGCATCATGATAATAGGCAGCAGACCAGAAGGCAA
AAAAAAAAAAAAAAAAAAGAGTTCTTCATCGCTTTGATCTGACCATCTATCTCTTCAAC
CATGGCCCATGGGGCAATCCTAACTGGAACCCAGAAATAAGCCGCCCCCTTCCTTAAGCT
AGACAGAAGAAGACGCCCATTATAGTGTCTAATAACGGTGTTAATTAAGTTGAGTAGTAG
CATGCATGAATACTATCGGGAAGAATATGTCAGATATTGCTGAAAGCATGTAATTAAGTT
GAGTAGCGGCATGCATGAATCTAGGGCCAGCAAGTCTGACCCGGACGGGCGGACCGGAGA
GGGCTCTCCCTCTCCAACAGTCCAACTACTACCGCAACTGTCAACGCAAGGCATAGGCAT
CCAAAACTGAAGATGAACGATACCTAACACCCCTGCATTAGTGCACAACTTCGTTGTCG
TCTTGCTGCCGTCATGTACTCGATTAGTCTAATTGTGTCTAGCCATTGGACGTGAAGAAA
AAGGTTCTCCTCCTTCCCTTGTGCCAAAATAAATAAATAAACGAAGGGCAAAGGGCAAGA
TCAAGCGAGTGGTCACGATCAGAGGTGTACAGTACAGTTGTACATGCATGTTTCTGGAAT
CTGATCAGTGGACTCGGAGTGCGAATCAATCAGTCAAGGTGCTAAAAGAAGCTACAAAT
GTGCACGCTTCTTCATCTTGTGCATCCCATTCTGTGTGAGAAAGAGAGAGAGAGAGAGAG
```

FIG. 4 CONTINUED

```
AGAGAGAGAGAGAGAGAGAGAGAGAGAGAGAGAGAGAGAGAGAGAGAGAGAGAGGTGA
ATGGCACACTTCTAGCAAGTTCTTGTAGCACGGACAACGAAAGGGTGAGCTTTGAAAAGT
ACACTCCACGAAGGATATGCAAAAAAATGAAATAGGCCCGAAAGTTCAATTAGACAGTCC
AATTCCGAAGCACCCACAAATTGGTTGTTGGCCCATGAAGCACCCACAACACCCTGTATC
TCGTCCAGCCCACTTTGCATCCAATCCAACGGCAACGGGCAACGAAATGGCACCGTGTTA
CACGAACACGCGTCACACGACGGGAATGTCAGAAGTCAGAACAGCTCGTTCGTCCGTCAC
CAACTCGCCATAGATGATAGAACGCTATCCCATCTTCACACACAAAAATATCCGCGCGAC
CCCGACCTCCCCCCTCCCACTCCGGGCAGCAGCCAGCAGCCAGCAGGCATGGGGATACCC
GTGGTGGTTCCCGTCGCGGCGGCCTACTCGTGCTCCTCCTCCCTCGCCGCGCCACCGAGG
GCCGCCGCCGCCGCGGCGAGGGCGCCGAGCCGCGCACGTCGCGGCGGCCGGGATGTCC
TCCAGGGCGTCCTCCTTCGTCGGGGGCAGCGGAGGCGACCTCGCGGCGGTGGCCGCGTCG
GTAGCCGCGCGGCCCAGGAGGGCGGGCTCCGGGGGAGGCGGCGCGCTCGGGTGCAAGTGC
CTCTTCGGGCTCGGCGTGCCGGAGCTCGCCGTCATCGCCGGCGTCGCCGCGCTCGTGTTC
GGGCCCAAGCAGCTCCCCGAGATCGGCCGCAGCATCGGCAAGACCGTCAAGAGCTTCCAG
CAGGTGAGGGTTGGGGCATGAATCCAAATGGCGTGGTCAGTAGAAGCTCGCGGTTGCTGG
GGGGGCGATGCTGACAATCGTTTGACTGCTAGTTAGCAGCTGCGGAAACTTGTCACCCCG
TTTTGCTCGAGATGCTAAAGCTTAGGTCTTCTTCGTAGTGTTACCAATCTGCAAGTCATT
GCTTTGGTAGCTATGAATATGCAGGCGGAGGAAGTATCCTCACCCCCACACCCCCGGCGC
GCTGAACCGTATAAAAAAAGTTTGGCTGATTTCGGTACTCTAGTAGATAATATTGTTCAG
TTTGGCAGCTAATACAGTGGCCCAGTAAATCACATTCATTGCAAATTTGCATTTTGGCTC
GGCTGTGCTGTTGACCGCTTAGTGGGATGCCAATGGTAGGATATATGGCCACATTGCTTC
CTCATTTTGACTTATGAGCAGTGTTCTTAAGGCGCCTAGGCGAGCAAGCAAACACTCCGA
GCGCCTTAGCGCCTACGCGGGCAAGGCGGCAAGGTTTAGCCGAGCGCCCGCCTAGGCGAC
GCCTTAAAAACCCTGCTTATGAGTTATGTTTTTTATATGCCAGTGTGATGAGTGGTGTG
GGTACAGGGATGTAAGATTGGAGTGATAGAAATTTCTGCACCTCATTCTTTCTGAACTGC
AATGGGAAGTAGTAGAACATATCTTCCAATTTAGTACTACCTCTTGTCGGATTTAGGTGA
CGTTTTGGAAAATCAAAAAGATTGGAGCAAGTAGTTGTTTGAGATGGAGCCAAAATTTGG
TGTGGTTTGTTCTTGCCCATTTGGAGTTGTATAATCTCTTAAGAGTCCTGCATGTTATGA
TATGTGCAGGGTTTTTTTGGTCGCCGATGAATTATGTCATATACAAGCTAGGCCTGTAG
CTGTAGCAAAGATAACAGTTGTTACCTTTAGGGCCTATTTGGAAGCTCTGTAATTTCCTA
GTTTCAAGGTAATACTGTAGTATTGGAGAATACCATAGTTTTATAGGCTAAAAGGTGTTT
GGTTGGTCCTTTCAAAACTCTGTTTTCAATACTATGGTTTGTCAATACTATAGAATTTTT
GTGGTGTTGGATACTTCAATCTTGACCCAAGTTTTCTTTGCGCAAGAGCAGCTCGCAGCA
CACAGAATAATGGAAACAAACACACTTCGGTTTCAAAAAAATACCATGGTTTAAATAGAG
TAATCGAAACTACAGTATTCATGTCACAACCAAAAAAATGCTATTGTATTCTAAAACCAC
AGTATTAGAAAACAATGCTGCCAAACAGGCCTTACGTGTTAGAGTGTTACCTATTGAGAT
TCAGCTGACTTTACATTTATTATAAAATGATAACCCCACGATGCTAAATTTTCATTGCTT
TTAAAATCAAGAAGGGGGTAATTGTCTTGAGAATAGTCCCACATTGTGTGTTGTGGAGAA
GCAATCATGGTTTATATGTTTGAGGGTGCAAGTGCAACCCCCTAATGGGCAAGCCTTTTG
GGGGGAGTATTGGCCCAACAGACCTAAAGCCCGCTGCTATGCGTGCGTGCGCGTGTGTCG
CGGCCCGATGACTTGGATAGGCGCGCCGTGTGGTGGGTGGCCCGACGGACACGCCATGTG
TTGGTGGTTCAGTTTAGGTCCGGTTCCAACAATTGGTATCAAAGCCAGATTGACCCAGTG
TATTCTCAGACAAATCTCGGCTCACAATGTGTGAGGGAGAGATTGTTGAGAATAGTCCCA
CATAGTGGGTGCACCCCCCTAATGGGTTAGCTTTTTGGAGAGTATTGGCCCAACAGACC
TAAATCTCGCTGTCATGTGTGCGGACGCGTGTGTCGCGGCCTGACAGCCTTGGTAGGCGC
GCTGTATGTGCGGATACGCCATGTGTCGGCGGTCCGGTTCCAACAAATTGGTCTAAAACT
GAGGCCATTTGTGGTTTATGATCTATGTTTTGGTCGTTGCCAACTTACATGCTGATATGG
CTTACCCAATTCTACTTGATAGGAGATAAAGCTGCAGAGAAGAAATGGTTTAAAGGTGGC
GTGTAAAAGTTGAAAAGTGTTTCCATTTTAGTCCAACTTGTTTTAGGAGGCAGGGTGTGC
GGAAATTAGTGTCTAGAGACTAGAGATATGTCACCCACAGGCCACAGGGCCACATTACCA
CTAGTTTGATAATTTCATCATTACTTAGAAGAATGATATGCCTGCTTCCTTTTGGTCTCA
CTTGTCTAAGAATTTGATGGGACTGATCCACCTTAGCCTGCACCATTATACTAATTGAAA
GCTTGTTGAGTTGCATACACTTCGTGCTCTGTTTCTGAAGATCAAGTTTTCTGACCAGCA
TTATTTCCTTTTCCATTCAGTAAAATTGTTCCGTGATCCATCCAACTTCTCTCGCAGGCG
GCTAAGGAGTTTGAAACTGAACTGAAGAAAGAGCCTGGGGAAGGCGGCGATCAGCCCCCA
CCTGCAACTCCCACAGCTGTAAGTGGCGGGGAGGAGAAGGGGCTTGAGGCATCTAGTAGC
AAGGAGAGCGCGTGAGGATCAGGATCTATCTAGTGTTGTTTATGAAAATTGTATTCTGGG
CTTCTCGAGTTAGCAGTTCATATCCTTTTAACCGCATCGCGGTTTCAGGCCATGTAGCGA
TATTGTTTGTAGTTTGTACCGGGAATAACATATTTGGTTGAGCTTCTACGTATTGAAGAA
ACAACTTATCTGTGAAGCTGACGCGAACAA
```

MUTATION OF THE ZMCIPK15 GENE TO INCREASE ROOT ANGLE AND TO ENHANCE ABIOTIC STRESS TOLERANCE IN MAIZE

CROSS-REFERENCE TO RELATED APPLICATIONS

This application claims the benefit of U.S. Provisional Patent Application 62/584,442 filed Nov. 10, 2017, which is incorporated herein as if set forth in its entirety.

STATEMENT AS TO RIGHTS TO INVENTIONS MADE UNDER FEDERALLY SPONSORED RESEARCH AND DEVELOPMENT

This invention was made with government support under IOS0965380 awarded by the National Science Foundation and 2014-67013-21572 awarded by the USDA/NIFA. The government has certain rights in the invention.

FIELD OF THE INVENTION

The present invention relates to crop breeding. More particularly, the present invention relates to targeted modification of maize root to enhance abiotic stress tolerance.

BACKGROUND OF THE INVENTION

Improvements in the yield of cereal crops such as wheat and maize have recently plateaued[3]. This is a major cause for concern with respect to food security, particularly given projected global population growth and the impacts of climate change on crop productivity. In intensive agricultural systems, intensive fertilization and irrigation cause environmental degradation and are not sustainable in the long term, while in the low-input agriculture characteristic of developing nations, limited availability of water and nutrients are primary limitations to crop production[4,5]. Therefore, crops and crop varieties with greater resource efficiency and climate resilience are urgently needed in global agriculture.

Plant productivity is often limited by suboptimal nutrient and water availability in natural and managed ecosystems. Root architectural phenes have the potential to improve plant performance under edaphic stresses by improving the metabolic efficiency of soil exploration and by optimizing root foraging in specific soil domains[1,2]. Root architectural phenes, including root growth angle, influence root distribution, plant performance, and soil resource acquisition under nutrient and water stress conditions[2-5]. Root growth angle affects rooting depth in maize[3], rice[6], sorghum[7], common bean[8], and wheat[9]. A shallow root system enhances topsoil exploration, thereby improving exploitation of immobile resources such as phosphorus, as demonstrated in maize[10], soybean[8], and common bean[11]. In contrast, plants with steep root angles are better suited to capture mobile resources such as nitrate and water, which move to deep soil domains over time[2,3]. Root angle affects the timing and amount of water extraction from the soil in rice and wheat[12,13] and reduced soil water availability in wheat resulted in steeper root angles[14]. Under nitrogen deficient conditions, maize nodal root growth angles become steeper, which enables the exploration of deeper soil domains with the greatest nitrogen availability[3].

Root angle has received little attention in plant breeding due to the challenges of excavating and phenotyping mature root systems from soil. Many root quantitative trait loci (QTL) studies have been limited by artificial growth systems[16,17] and phenotyping embryonic root systems[17,18]. In artificial growth systems root elongation and trajectory can be affected by several factors including root constriction, root interface with container surfaces, and media that present unrealistic physical, chemical, and microbiological regimes. Embryonic root systems are poor predictors of mature root system architecture[19], may be under distinct genetic control from post-embryonic root systems[20], and are influenced by maternal provisioning.

In view of the current state of the crop breeding industry, particularly new maize varieties, it can be appreciated that identifying genes conveying abiotic stress tolerance is a substantial challenge in the field. Accordingly, a need exists in the field to identify additional genes that influence stress tolerance.

SUMMARY OF THE INVENTION

This invention is based, in part, on the Inventors' discovery of a maize gene named GRMZM2G472643 in B73 RefGen_v3 5b+ of the maize genome annotation and named ZEAMMB73_Zm00001d03316 in maize assembly version Zm-B73-REFERENCE-GRAMENE-4.0 of the maize genome annotation. (Note: Use of either of these terms in this document are used to indicate the same gene.) This gene affects the angle of root growth. Root systems with steeper angles reach depth more quickly and ultimately grow more deeply in the soil. Deeper roots acquire nitrogen more efficiently and acquire water longer in the growing season. Therefore, stress tolerant plants with steeper root angles can be grown and deeper root systems of sequestering carbon in the soil. The inventors have demonstrated in the Examples that a reduction of gene function results in increased root angle. Accordingly, this invention has value as an approach to improve yield under stress tolerance and increase soil carbon sequestration.

In a first aspect, provided herein is a maize plant, comprising a non-natural mutation that modulates the function of maize gene GRMZM2G472643, wherein the maize plant exhibits altered root angle as compared to a maize plant lacking said mutation. In some embodiments, the maize plant is selected from the group consisting of a corn-belt dent maize germplasm, a maize inbred and a maize hybrid. In some embodiments, the maize plant is selected from the group consisting of the following lines: W22, Hill, and B73. In some embodiments, the maize root angle is altered by at least 2 degrees. In some embodiments, the maize root angle is altered by between 2 and 80 degrees. In some embodiments, the maize plant is a recombinant maize plant.

In a second aspect, provided herein is a maize plant tolerant of abiotic stress, comprising a non-natural mutation that decreases the function of maize gene GRMZM2G472643, wherein the maize plant exhibits increased root angle and increased abiotic stress tolerance as compared to a maize plant lacking said mutation. In some embodiments, the increase in root angle is at least 2 degrees. In some embodiment, the increase in root angle is between 2 and 80 degrees. In some embodiments, the non-natural mutation comprises an increase in the number of GRMZM2G472643 copies in the plant. In some embodiments, the non-natural mutation comprises a modification of sequences regulating GRMZM2G472643.

In a third aspect, provided herein is a method of increasing abiotic stress tolerance in maize, comprising introducing in maize a non-natural mutation that decreases the function of maize gene GRMZM2G472643, wherein said maize exhibits increased abiotic stress tolerance as compared to maize lacking said mutation.

In a forth aspect, provided herein is a method of increasing root angle in maize, comprising introducing in maize a non-natural mutation that decrease the function of maize gene GRMZM2G472643, wherein said maize exhibits increased root angle as compared to maize lacking said mutation.

In a fifth aspect, provided herein is a method of identifying an abiotic stress tolerant maize plant, comprising: (a) assaying expression levels of a maize gene GRMZM2G472643 in maize plants; and (b) selecting a maize plant having a decreased level of maize gene GRMZM2G472643 expression, wherein said selected maize plant exhibits increased abiotic stress tolerance as compared to a maize plant not having the decreased level of maize gene GRMZM2G472643 expression.

In a sixth aspect, provided herein is a method for providing an abiotic stress tolerant maize plant variety, comprising: (a) assaying expression levels of maize gene GRMZM2G472643 in maize plants; (b) selecting a maize plant exhibiting increased levels of maize gene GRMZM2G472643 expression; and (c) breeding said selected maize plant exhibiting increased levels of maize gene GRMZM2G472643 to yield a maize plant variety providing increased tolerance to abiotic stress.

Other objects, features and advantages of the present invention will become apparent after review of the specification, claims and drawings. The detailed description and examples enhance the understanding of the invention, but are not intended to limit the scope of the appended claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A shows shovelomics soil monolith containing maize root crown before low pressure washing. FIG. 1B shows maize root crown demonstrating the measure of crown root angle. FIG. 1C show variation in brace root angle in the Wisconsin Diversity panel in four field environments. FIG. 1D shows variation in crown root angle in the Wisconsin Diversity panel in four field environments. FIG. 1E shows variation in crown root angle in maize ranging from shallow angle to steep angle. FIG. 1F shows genome-wide association study (GWAS) was performed on root angle data. A Manhattan plot describes GWAS results from crown root angle analysis. FIG. 1G QQ plot demonstrating a good model fit.

FIG. 2A shows a Manhattan plot of genome-wide association study results for crown root angle. Chromosome-wide significance threshold ($-\log_{10}p=5.73$) was determined through the simpleM multiple testing correction method. The significant SNPs is located in the gene model GRMZM2G472643 encoding a CBL serine/threonine protein kinase. SNPs within this gene model are indicated by green dots. FIG. 2B shows expansion of Manhattan plot for chromosome one, highlighting gene model GRMZM2G472643 in green. The most significant SNP was located at position 253272442 bp on chromosome one. FIG. 2C shows relative expression on CIPK15 in various root tissues. FIG. 2D shows a schematic diagram for CIPK15 gene model. Introns are represented in gray and exons are represented in black.

FIGS. 3A and 3B show root crowns of wildtype (WT) and CIPK15 (Uniform Mu insertion line). FIG. 3C shows SimRoot simulations demonstrated that there was no significant differences in nitrate uptake between the WT and zmcipk15 in high nitrogen conditions. The zmcipk15 mutant had significantly greater nitrate uptake compare to WT in low nitrogen conditions. FIG. 3D shows field studies from three environments demonstrating that zmcipk15 had significantly greater nitrogen uptake in low nitrogen conditions compared to wildtype. FIG. 3E shows SimRoot simulations demonstrated that there was no significant differences in shoot dry weight between the WT and zmcipk15 in high nitrogen conditions. The zmcipk15 mutant had significantly greater shoot dry weight compare to WT in low nitrogen conditions. Significance levels (NS, not significant; *, $p<0.15$; , $p<0.1$; *, $p<0.05$) are shown. FIG. 3F shows field studies demonstrating that zmcipk15 had greater shoot biomass in low nitrogen conditions compared to wildtype. FIG. 3G shows greenhouse study results comparing the zmcipk15 mutant and WT. Mutants harboring the zmcipk15 gene demonstrated a significantly steeper root angles at whorl two and four. Significance levels (NS, not significant; *, $p<0.15$; , $p<0.1$; *, $p<0.05$) are shown. FIG. 3H shows root crowns of wildtype (WT) and CIPK15 (Uniform Mu insertion line). FIG. 3H also shows field study results from three environments comparing the zmcipk15 mutant and WT. Mutants harboring the zmcipk15 gene demonstrated a significantly steeper root angles at whorl two and three. Significance levels (NS, not significant; *, $p<0.15$; , $p<0.1$; *, $p<0.05$) are shown.

FIG. 4 shows the genomic DNA sequence of the gene model based on B73 RefGen_v3 and shows the sequence from Zm-B73-REFERENCE-GRAMENE-4.0 including gene model at coordinates 258845263 . . . 258848552 and 5.0 kb upstream and downstream of the gene model.

DETAILED DESCRIPTION OF THE INVENTION

Figures 1A, 1B, 1C, 1D, 1E, 1F, 1G:
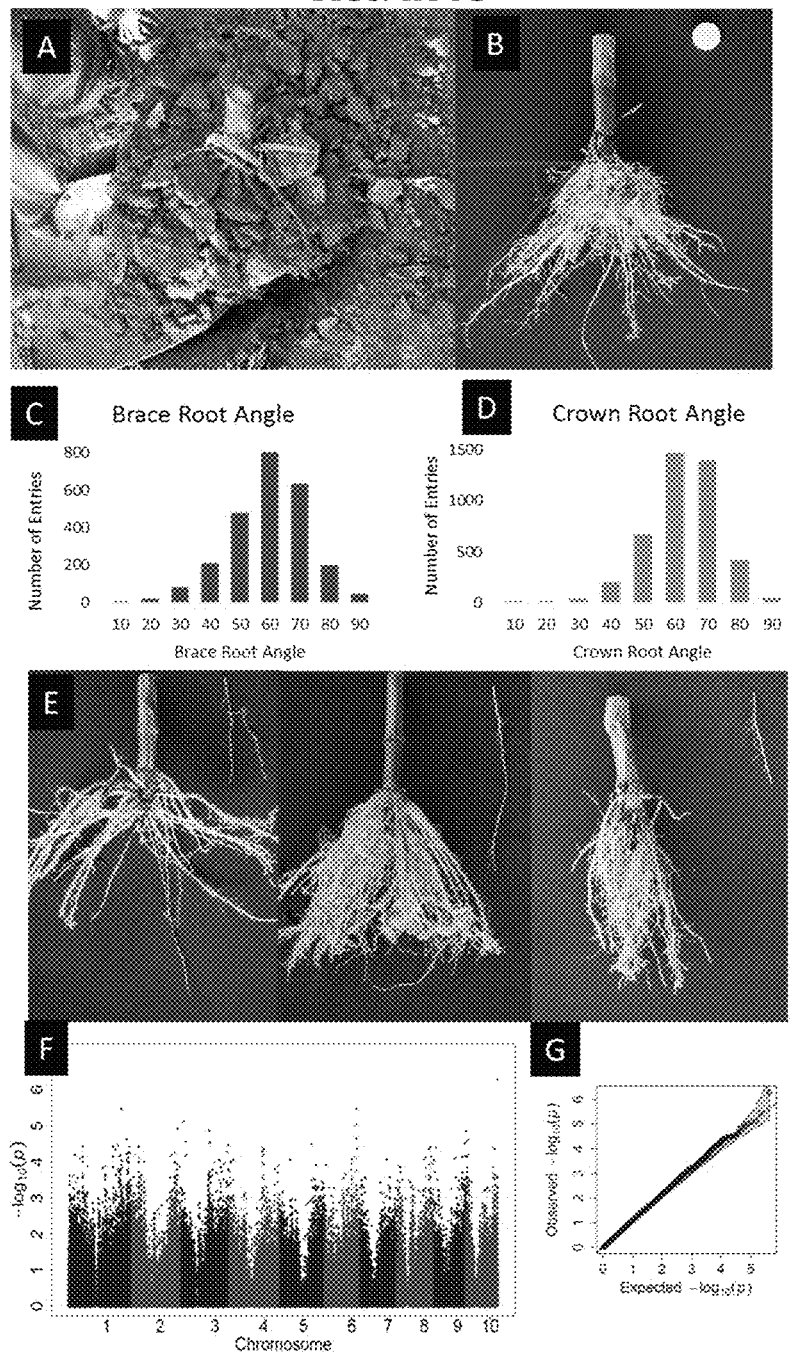
FIGS. 1A-1G show the shovelomics pipline for maize.

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention, which will be limited only by the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, cell lines, vectors, animals, instruments, statistical analysis and methodologies which are reported in the publications which might be used in connection with the invention. All references cited in this specification are to be taken as indicative of the level of skill in the art.

The practice of the present invention will employ, unless otherwise indicated, conventional techniques of molecular biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); and Handbook Of Experimental Immunology, Volumes I-IV (D. M. Weir and C. C. Blackwell, eds., 1986).

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters that cause a gene to be expressed in most cell types at most times are commonly referred to as "constitutive promoters". Promoters that allow the selective expression of a gene in most cell types are referred to as "inducible promoters".

A "host cell" is a cell which has been transformed or transfected, or is capable of transformation or transfection by an exogenous polynucleotide sequence. A host cell that has been transformed or transfected may be more specifically referred to as a "recombinant host cell".

The nucleic acid sequence for the target gene, GRMZM2G472643, is recited in SEQ ID NO: 1 and also recited in FIG. 4.

By "modulation" of the target gene, we mean to include both over-expression and under-expression. In a preferred version of the present invention, the gene is over-expressed. By "modulation of the gene," we also mean to include modification or manipulation of the regulatory regions of the target gene.

By "a non-natural mutation," we mean to include all manner of recombinant, transgenic manipulation, and gene-editing to the plant which does not occur in nature and requires the hand of man. For example, a plant comprising an extra copy of the target gene has a non-natural mutation. A plant comprising a vector containing the target gene and a promoter from a different maize or plant line is a non-natural mutation. We also mean to include modification or manipulation of the regulatory regions of the target gene or of any region that is contiguous with the target gene up to 5 KB on either side of the target sequence, such as modifications, mutations or substitutions of the promoter region. Non-natural mutations may also include epigenetic modifications or manipulations. In some embodiments, the non-natural mutation may be a gene-editing modification for the upregulation or down-regulation of the target gene. In some embodiments, the non-natural mutation is a genetic modification selected from the group consisting of a disruption or mutation in the promoter sequence of the target gene, a frame shift mutation, based modification in the gene or promoter region, altering epigenetic function, deletion of the gene, or a CRISPR-Cas9 knock out of the target gene to decrease expression. In some embodiments, the non-natural mutation is a transposon-tagged mutation harboring a Uniform Mu transposon insertion in an exon of the target gene. Suitable gene-editing methods are known in the art. For example, see Kamburova et al. ("Genome editing in plants: an overview of tools and applications," International Journal of Agronomy, 2017) which is incorporated herein by reference.

A polypeptide "substantially identical" to a comparative polypeptide varies from the comparative polypeptide, but has at least 80%, preferably at least 85%, more preferably at least 90%, and yet more preferably at least 95% sequence identity at the amino acid level over the complete amino acid sequence, and retains substantially the same biological function as the corresponding polypeptide to which comparison is made.

The term "substantial sequence homology" refers to DNA or RNA sequences that have de minimus sequence variations from, and retain substantially the same biological functions as the corresponding sequences to which comparison is made.

As used herein, "hybridizes under stringent conditions" is intended to describe conditions for hybridization and washing under which nucleotide sequences that are significantly identical or homologous to each other remain hybridized to each other. Such stringent conditions are known to those skilled in the art and can be found in Current Protocols in Molecular Biology, Ausubel et al., eds., John Wiley & Sons, Inc. (1995), sections 2, 4 and 6. Additional stringent conditions can be found in Molecular Cloning: A Laboratory Manual, Sambrook et al., Cold Spring Harbor Press, Cold Spring Harbor, N.Y. (1989), chapters 7, 9 and 11. A preferred, non-limiting example of stringent hybridization conditions includes hybridization in 4× sodium chlorine/sodium citrate (SSC), at about 65-70° C. (or hybridization in 4×SSC plus 50% formamide at about 42-50° C.) followed by one or more washes in 1×SSC, at about 65-70° C. A preferred, non-limiting example of highly stringent hybridization conditions includes hybridization in 1×SSC, at about 65-70° C. (or hybridization in 4×SSC plus 50% formamide at about 42-50° C.) followed by one or more washes in 0.3×SSC, at about 65-70° C. A preferred, non-limiting example of highly stringent hybridization conditions includes hybridization in 4×SSC, at about 50-60° C. (or alternatively hybridization in 6×SSC plus 50% formamide at about 40-45° C.) followed by one or more washes in 2×SSC, at about 50-60° C. Ranges intermediate to the above-recited values, e.g., at 65-70° C. or at 42-50° C. are also intended to be encompassed by the present invention. SSPE (1×SSPE is 0.15 M NaCl, 10 mM $NaH_2PO_4$, and 1.25 mM EDTA, pH 7.4) can be substituted for SSC (1×SSPE is 0.15 M NaCl and 15 mM sodium citrate) in the hybridization and wash buffers; washes are performed for 15 minutes each after hybridization is complete. The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m$ (° C.)=2(# of A+T bases)+4(# of G+C bases). For hybrids between 18 and 49 base pairs in length, $T_m$ (° C.)=81.5+16.6($\log_{10}$[Na+])+0.41(% G+C)−(600/N), where N is the number of bases in the hybrid, and [Na+] is the concentration of sodium ions in the hybridization buffer ([Na+] for 1×SSC=0.165 M). It will also be recognized by the skilled practitioner that additional reagents may be added to the hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS) chelating agents (e.g., EDTA), Ficoll, PVP and the like. When using nylon membranes, in particular, an additional preferred, non-limiting example of stringent hybridization conditions is hybridization in 0.25-0.5M $NaH_2PO_4$, 7% SDS at about 65° C., followed by one or more washed at 0.02M $NaH_2PO_4$, 1% SDS at 65° C., see e.g., Church and Gilbert (1984) Proc. Natl. Acad. Sci. USA 81: 1991-1995, (or alternatively 0.2×SSC, 1% SDS).

"Polynucleotide(s)" generally refers to any polyribonucleotide or polydeoxyribonucleotide, which may be unmodified RNA or DNA or modified RNA or DNA. "Polynucleotide(s)" include, without limitation, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded regions, or a mixture of single- and double-stranded regions. As used herein, the term "polynucleotide(s)" also includes DNAs or RNAs as described above that contain one or more modified bases. Thus, DNAs or RNAs with backbones modified for stability or for other reasons are "polynucleotide(s)" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term "polynucleotide(s)" as it is employed herein embraces such chemically, enzymatically or metabolically modified forms of polynucleotides, as well as the chemical forms of DNA and RNA characteristic of viruses and cells, including, for example, simple and complex cells. "Polynucleotide(s)" also embraces short polynucleotides often referred to as oligonucleotide(s).

The term "isolated nucleic acid" used in the specification and claims means a nucleic acid isolated from its natural environment or prepared using synthetic methods such as those known to one of ordinary skill in the art. Complete purification is not required in either case. The nucleic acids of the invention can be isolated and purified from normally associated material in conventional ways such that in the purified preparation the nucleic acid is the predominant species in the preparation. At the very least, the degree of purification is such that the extraneous material in the preparation does not interfere with use of the nucleic acid of the invention in the manner disclosed herein. The nucleic acid is preferably at least about 85% pure, more preferably at least about 95% pure and most preferably at least about 99% pure.

Further, an isolated nucleic acid has a structure that is not identical to that of any naturally occurring nucleic acid or to that of any fragment of a naturally occurring genomic nucleic acid spanning more than three separate genes. An isolated nucleic acid also includes, without limitation, (a) a nucleic acid having a sequence of a naturally occurring genomic or extrachromosomal nucleic acid molecule but which is not flanked by the coding sequences that flank the sequence in its natural position; (b) a nucleic acid incorporated into a vector or into a prokaryote or eukaryote genome such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene. Specifically excluded from this definition are nucleic acids present in mixtures of clones, e.g., as those occurring in a DNA library such as a cDNA or genomic DNA library. An isolated nucleic acid can be modified or unmodified DNA or RNA, whether fully or partially single-stranded or double-stranded or even triple-stranded. A nucleic acid can be chemically or enzymatically modified and can include so-called non-standard bases such as inosine, as described in a preceding definition.

The term "operably linked" means that the linkage (e.g., DNA segment) between the DNA segments so linked is such that the described effect of one of the linked segments on the other is capable of occurring. "Linked" shall refer to physically adjoined segments and, more broadly, to segments which are spatially contained relative to each other such that the described effect is capable of occurring (e.g., DNA segments may be present on two separate plasmids but contained within a cell such that the described effect is nonetheless achieved). Effecting operable linkages for the various purposes stated herein is well within the skill of those of ordinary skill in the art, particularly with the teaching of the instant specification.

As used herein the term "gene product" shall refer to the biochemical material, either RNA or protein, resulting from expression of a gene.

The term "heterologous" is used for any combination of DNA sequences that is not normally found intimately associated in nature (e.g., a green fluorescent protein (GFP) reporter gene operably linked to a SV40 promoter). A "heterologous gene" shall refer to a gene not naturally present in a host cell (e.g., a luciferase gene present in a retinoblastoma cell line).

As used herein, the term "homolog" refers to a gene related to a second gene by descent from a common ancestral DNA sequence. The term, homolog, may apply to the relationship between genes separated by the event of speciation (i.e., orthologs) or to the relationship between genes separated by the event of genetic duplication (i.e., paralogs). "Orthologs" are genes in different species that evolved from a common ancestral gene by speciation. Normally, orthologs retain the same function in the course of evolution. Identification of orthologs is important for reliable prediction of gene function in newly sequenced genomes. "Paralogs" are genes related by duplication within a genome. Orthologs retain the same function in the course of evolution, whereas paralogs evolve new functions, even if these are related to the original one.

The nucleotides that occur in the various nucleotide sequences appearing herein have their usual single-letter designations (A, G, T, C or U) used routinely in the art. In the present specification and claims, references to Greek letters may either be written out as alpha, beta, etc. or the corresponding Greek letter symbols (e.g., α, β, etc.) may sometimes be used.

Nucleic acid constructs useful in the invention may be prepared in conventional ways, by isolating the desired genes from an appropriate host, by synthesizing all or a portion of the genes, or combinations thereof. Similarly, the regulatory signals, the transcriptional and translational initiation and termination regions, may be isolated from a natural source, be synthesized, or combinations thereof. The various fragments may be subjected to endonuclease digestion (restriction), ligation, sequencing, in vitro mutagenesis, primer repair, or the like. The various manipulations are well known in the literature and will be employed to achieve specific purposes.

The various nucleic acids and/or fragments thereof may be combined, cloned, isolated and sequenced in accordance with conventional ways. After each manipulation, the DNA fragment or combination of fragments may be inserted into a cloning vector, the vector transformed into a cloning host, e.g. *Escherichia coli*, the cloning host grown up, lysed, the plasmid isolated and the fragment analyzed by restriction analysis, sequencing, combinations thereof, or the like.

Various vectors may be employed during the course of development of the construct and transformation of host cells. The vectors may include cloning vectors, expression vectors, and vectors providing for integration into the host or the use of bare DNA for transformation and integration. The cloning vector will be characterized, for the most part, by having a replication original functional in the cloning host, a marker for selection of a host containing the cloning vector, may have one or more polylinkers, or additional sequences for insertion, selection, manipulation, ease of sequencing, excision, or the like. In addition, shuttle vectors may be employed, where the vector may have two or more origins of replication, which allows the vector to be replicated in more than one host, e.g. a prokaryotic host and a eukaryotic host.

Expression vectors will usually provide for insertion of a construct which includes the transcriptional and translational initiation region and termination region or the construct may lack one or both of the regulatory regions, which will be provided by the expression vector upon insertion of the sequence encoding the protein product. Thus, the construct may be inserted into a gene having functional transcriptional and translational regions, where the insertion is proximal to the 5'-terminus of the existing gene and the construct comes under the regulatory control of the existing regulatory regions. Normally, it would be desirable for the initiation codon to be 5' of the existing initiation codon, unless a fused product is acceptable, or the initiation codon is out of phase with the existing initiation codon. In other instances, expression vectors exist which have one or more restriction sites between the initiation and termination regulatory regions, so that the structural gene may be inserted at the restriction site(s) and be under the regulatory control of these regions.

Suitable methods for plant transformation for use with the current invention are believed to include virtually any method by which DNA can be introduced into a cell, such as by direct delivery of DNA by PEG-mediated transformation of protoplasts, by desiccation/inhibition-mediated DNA uptake by electroporation, by agitation with silicon carbide fibers, by *Agrobacterium*-mediated transformation, and by acceleration of DNA coated particles. Through the application of techniques such as these, maize cells, as well as those of virtually any other plant species, may be stably transformed, and these cells developed into transgenic plants.

Suitable Maize Lines

We envision that the present invention would be useful in all maize varieties and lines. Suitable maize lines may include, but are not limited to, corn-belt dent maize germplasm, maize inbreeds, and maize hybrids. Suitable maize lines are well known and well characterized in the art, such as, but not limited to, those described in Romay et al. (Comprehensive genotyping of the USA national maize inbred seed bank, Genome Biology, 2013, 14:R55), which is incorporated herein by reference. In some embodiments, the inbred maize line is selected from the group consisting of W22, Hill, and B73. In some embodiments, the maize hybrid is a tropical hybrid.

Figure 5:
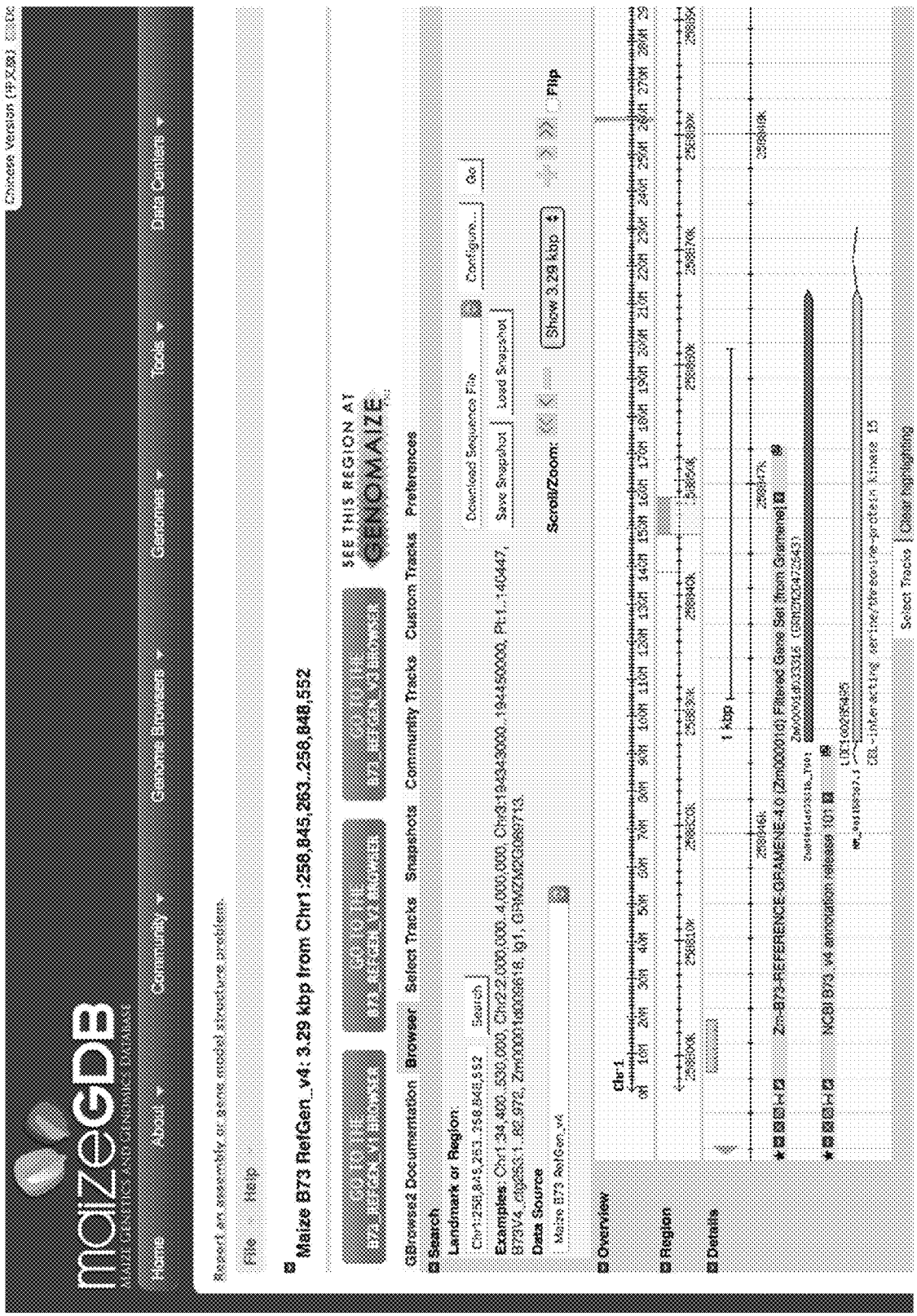
FIG. 5 shows a comparison between the gene annotation from GRMZM2G472643 from B73 RefGen_v2 annotation 5b and Zm-REFERENCE-GRAMENE-4.0 annotation Zm001d.2.
Figure 6:
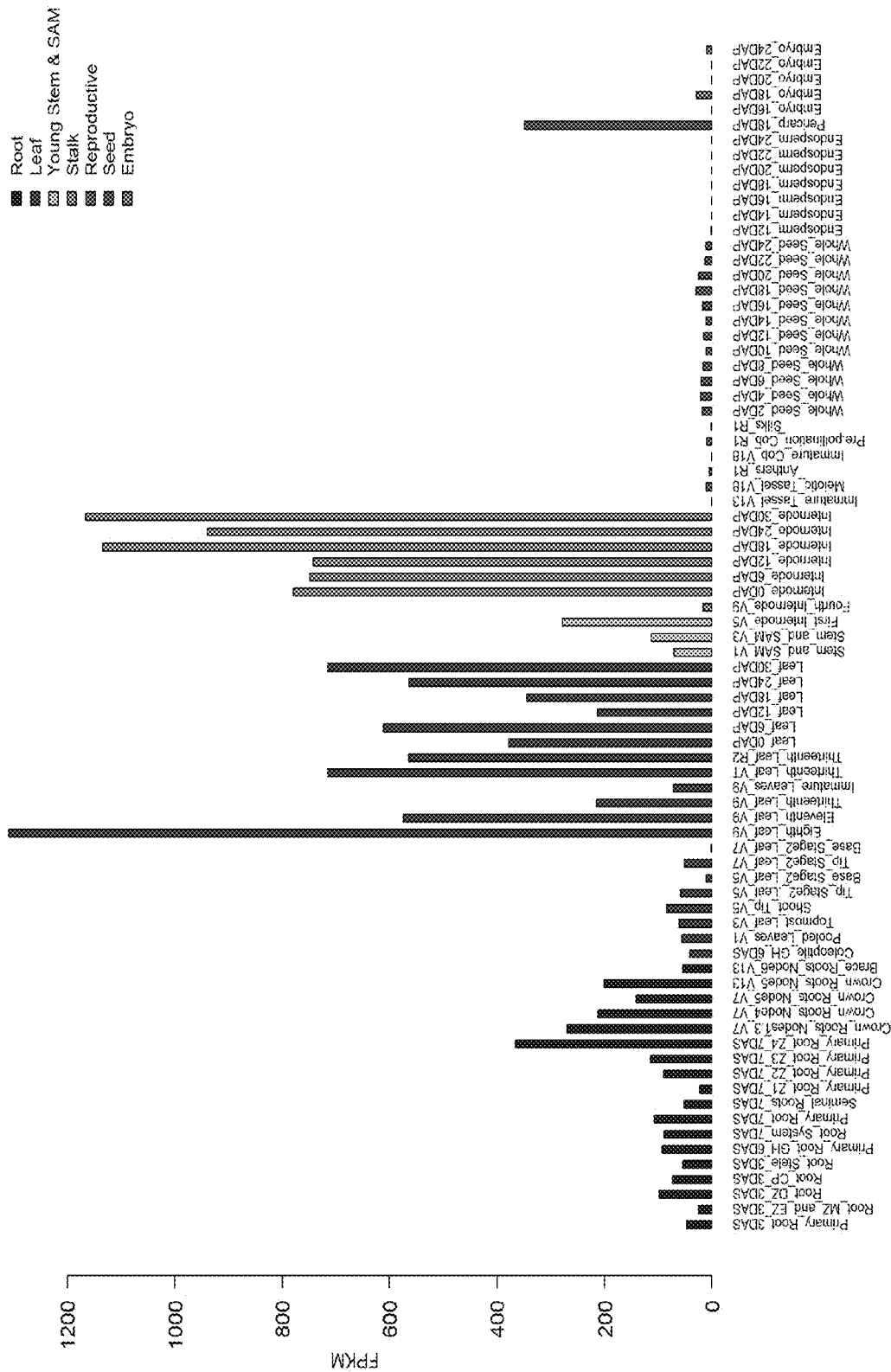
FIG. 6 shows spatial and temporal expression of CIPK15 based on the B73 maize gene atlas CITE SEKHON and STELPFLUG.
Figure 7:
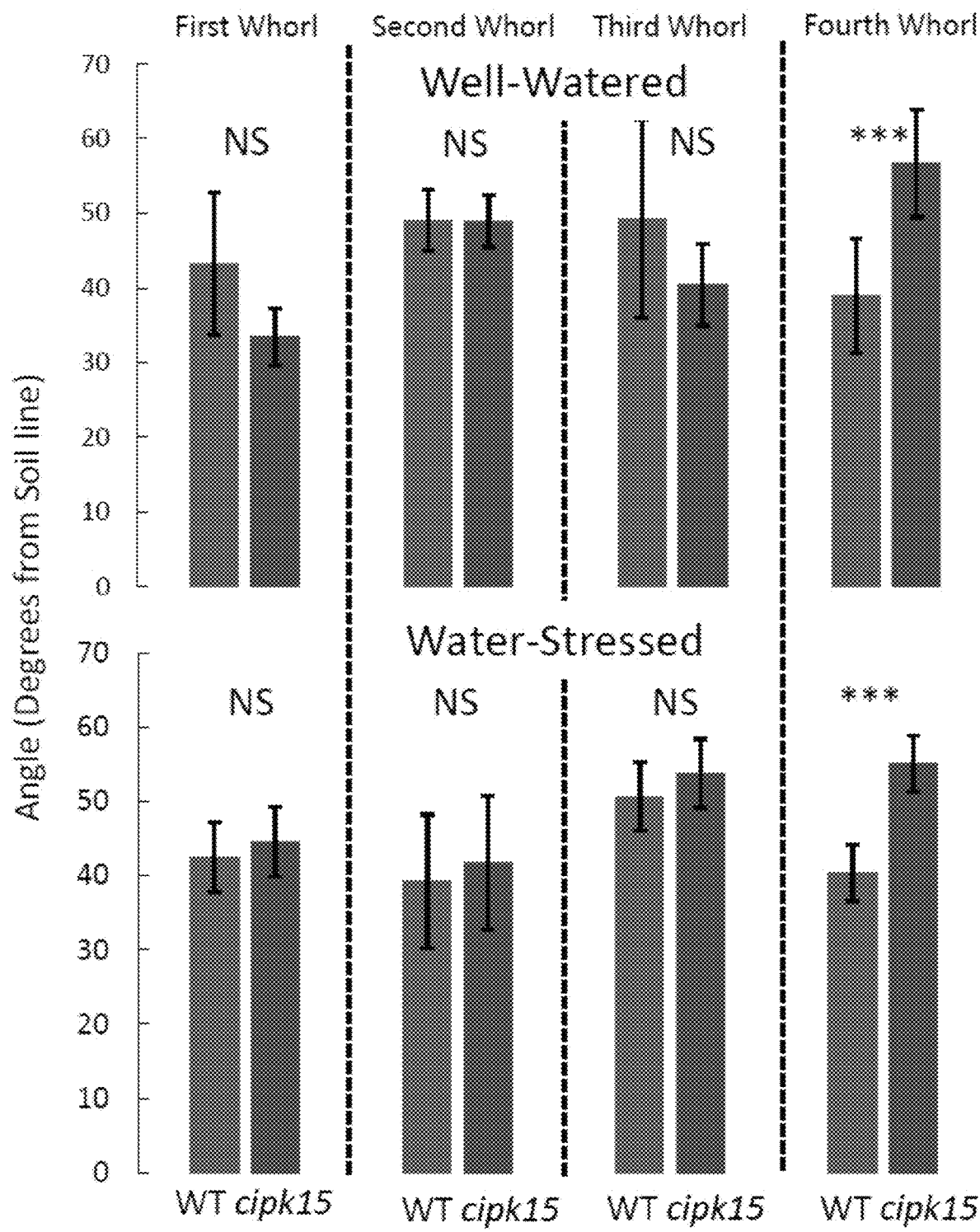
FIG. 7 shows phenotypic validation of the mutant locus associated with root angle in maize. Greenhouse study results comparing the zmcipk15 mutant and WT. Mutants harboring the zmcipk15 gene demonstrated a significantly steeper root angles at whorl four in well-watered and water-stressed conditions. Significance levels (NS, not significant; *, $p<0.15$; , $p<0.1$; * $p<0.05$) are shown.

We note that the conventions of expressing genetic positions in maize have changed. See FIG. 5. Initial work on this invention was done using the Maize B73 reference assembly B73 RefGen_v2 and annotation 5b. Recently, assembly Zm-REFERENCE-GRAMENE-4.0 with annotation Zm001d.2 has become available. The region of interest in this application is largely identical between the two versions, and nomenclature of GRMZM2G472643 from B73 RefGen_v2 annotation 5b and ZEAMMB73 Zm00001d03316 from Zm-REFERENCE-GRAMENE-4.0 annotation Zm001d.2 are considered to be referencing the same gene.

Increase in Gene Expression

The present invention, in certain aspects, includes steps of increasing the function of the target gene to yield a desirable phenotype. To that end, DNA may be introduced into the plant or plant cell to enable over-expression of GRMZM2G472643 and a decrease in root angle. Typically, the decrease in root angle would be decrease of at least 2 degrees (i.e., at least about 3 degrees, about 5 degrees, about 8 degrees, about 10 degrees, about 15 degrees, about 20 degrees, about 30 degrees or about 40 degrees). In some embodiments the decrease in root angle is between about 2 degrees and about 80 degrees (i.e., between 3 degrees and 75 degrees, between 5 degrees and 70 degrees, between 10 degrees and 65 degrees, between 15 degrees and 60 degrees). In some embodiments, the increase in expression of GRMZM2G472643 will result in a maize plant wherein the root angle is between about 10 degree and about 80 degrees from the soil line. The increase in expression or function of GRMZM2G472643 and the corresponding decrease in root angle of 2 or more degrees may be desirable to obtain cultivars with shallower root systems for growth in conditions low in phosphorous and high in water abundance. In general, a decrease in root angle will result in a shallower root system.

This introduction could include transformation of maize cells with multiple copies of the gene, use of modified or natural promoters designed to over-express the gene, use of constitutive or tissue-specific promoters designed to focus expression is specific tissues or in a non-specific manner, and use of vectors to carry a copy or copies of the gene. One may also wish to transform plant cells with regulatory elements that will modify the native expression of GRMZM2G472643 or modify existing regulatory elements.

Suitable methods for transformation of plant or other cells for use with the current invention are believed to include virtually any method by which DNA can be introduced into a cell, such as by direct delivery of DNA such as by PEG-mediated transformation of protoplasts. These methods and their use are well known in the art. The most likely transgenic approach would typically be using tissue-specific promoters that are stronger than the endogenous version in the line that is targeted.

After effecting delivery of exogenous DNA to recipient cells, the next steps generally concern identifying the transformed cells for further culturing and plant regeneration. In order to improve the ability to identify transformants, one may desire to employ a selectable or screenable marker gene with a transformation vector prepared in accordance with the invention. In this case, one would then generally assay the potentially transformed cell population by exposing the cells to a selective agent or agents, or one would screen the cells for the desired marker gene trait.

Cells that survive the exposure to the selective agent, or cells that have been scored positive in a screening assay, may be cultured in media that supports regeneration of plants. In an exemplary embodiment, MS media may be modified by including further substances such as growth regulators. Examples of such growth regulators are dicamba and 2,4-D. However, other growth regulators may be employed, including NAA, NAA+2,4-D or picloram. Media improvement in these and like ways has been found to facilitate the growth of cells at specific developmental stages. Tissue may be maintained on a basic media with growth regulators until sufficient tissue is available to begin plant regeneration efforts, or following repeated rounds of manual selection, until the morphology of the tissue is suitable for regeneration, then transferred to media conducive to maturation of embryoids. Cultures are transferred as needed on this medium. Shoot development will signal the time to transfer to medium lacking growth regulators.

The transformed cells, identified by selection or screening and cultured in an appropriate medium that supports regeneration, will then be allowed to mature into plants. Developing plantlets are transferred to soilless plant growth mix, and hardened, e.g., in an environmentally controlled chamber, for example, at about 85% relative humidity, 600 ppm $CO_2$, and 25-250 microeinsteins m−2 s−1 of light. Plants may be matured in a growth chamber or greenhouse. Plants can be regenerated from about 6 wk to 10 months after a transformant is identified, depending on the initial tissue. During regeneration, cells are grown on solid media in tissue culture vessels. Illustrative embodiments of such vessels are petri dishes and Plant Cons. Regenerating plants can be grown at a suitable temperature, for instance about 19 to 28° C. After the regenerating plants have reached the stage of shoot and root development, they may be transferred to a greenhouse for further growth and testing.

To confirm the presence of the exogenous DNA or "transgene(s)" in the regenerating plants, a variety of assays may be performed. Such assays include, for example, "molecular biological" assays, such as Southern and northern blotting and PCR™; "biochemical" assays, such as detecting the presence of a protein product, e.g., by immunological means (ELISAs and western blots) or by enzymatic function; plant part assays, such as leaf or root assays; and also, by analyzing the phenotype of the whole regenerated plant.

Very frequently the expression of a gene product is determined by evaluating the phenotypic results of its expression. These assays also may take many forms including but not limited to analyzing changes in the chemical composition, morphology, or physiological properties of the plant. Morphological changes may include ones known to demonstrate enhanced tolerance of abiotic stress, such as characterization of root system formation, characterization of root angle and measurement of carbon sequestrations. Most often changes in response of plants or plant parts to imposed treatments are evaluated under carefully controlled conditions termed bioassays.

One would typically assay for a suitable increase in gene expression resulting in increased RCA in the following ways:

Direct analysis of gene expression may be measured by one of various approaches to quantitative polymerase chain reaction, such as digital drop polymerase chain reaction. Variation in root angle may be measured by digital image analysis or direct sample analysis of maize root crowns collected from plants grown in the field or a controlled environment. In one embodiment, as demonstrated in Exhibit A, root angle is measured on crown and brace roots as the average degrees from horizontal measured from approximately 8 cm from the base of the stem. In some embodiments, root angle can be imaged or measured in the soil without excavating or harvesting the plant. The most practical measure of altered abiotic stress tolerance, or altered root system biomass, would be by excavation of all or representative portions of root systems grown in designed stress and control non-stress environments. Yield, yield components, plant biomass, plant health, and other traits would likely be measured in such field trials.

Decrease in Gene Expression

The present invention, in certain aspects, includes steps of reducing the function of a target gene GRMZM2G472643 to yield a desirable phenotype, such as increased root angle and deeper root system growth. To that end, DNA may be introduced into plants for the purpose of expressing RNA transcripts that function to affect plant phenotype yet are not translated into protein. Two examples are antisense RNA and RNA with ribozyme activity. Both may serve possible functions in reducing or eliminating expression of native or introduced plant genes. However, as detailed below, DNA need not be expressed to effect the phenotype of a plant. Typically, the increase in root angle would be an increase of at least 2 degrees (i.e., at least about 3 degrees, about 5 degrees, about 8 degrees, about 10 degrees, about 15 degrees, about 20 degrees, about 30 degrees or about 40 degrees). In some embodiments the increase in root angle is between about 2 degrees and about 80 degrees (i.e., between 3 degrees and 75 degrees, between 5 degrees and 70 degrees, between 10 degrees and 65 degrees, between 15 degrees and 60 degrees). In some embodiments, the decrease in expression of GRMZM2G472643 will result in a maize plant wherein the root angle is between about 10 degree and about 80 degrees from the soil line. The decrease in expression or function of GRMZM2G472643 and the corresponding increase in root angle of 2 or more degrees may be desirable to obtain cultivars with deeper root systems for growth in conditions low in nitrogen and low in water abundance. In general, an increase in root angle will result in a deeper root system. In some embodiments, root depth may be increased 1% to 80% (i.e, about 2%, 5%, 10%, 15%, 20%, 30%, 40%, 60%, 70%, 80%).

Genes may be constructed or isolated, which when transcribed, produce antisense RNA that is complementary to all or part(s) of a targeted messenger RNA(s). The antisense RNA reduces production of the polypeptide product of the messenger RNA. The polypeptide product may be any protein encoded by the plant genome. The aforementioned genes will be referred to as antisense genes. An antisense gene may thus be introduced into a plant by transformation methods to produce a novel transgenic plant with reduced expression of a selected protein of interest.

Genes also may be constructed or isolated, which when transcribed, produce RNA enzymes (ribozymes) which can act as endoribonucleases and catalyze the cleavage of RNA molecules with selected sequences. The cleavage of selected messenger RNAs can result in the reduced production of their encoded polypeptide products. These genes may be used to prepare novel transgenic plants which possess them. The transgenic plants may possess reduced levels of polypeptides including, but not limited to, the polypeptides cited above.

Ribozymes are RNA-protein complexes that cleave nucleic acids in a site-specific fashion. Ribozymes have specific catalytic domains that possess endonuclease activity. For example, a large number of ribozymes accelerate phosphoester transfer reactions with a high degree of specificity, often cleaving only one of several phosphoesters in an oligonucleotide substrate. This specificity has been attributed to the requirement that the substrate bind via specific base-pairing interactions to the internal guide sequence ("IGS") of the ribozyme prior to chemical reaction.

Several different ribozyme motifs have been described with RNA cleavage activity. Examples include sequences from the Group I self-splicing introns including Tobacco Ringspot Virus, Avocado Sunblotch Viroid, and Lucerne Transient Streak Virus. Sequences from these and related viruses are referred to as hammerhead ribozyme based on a predicted folded secondary structure.

Other suitable ribozymes include sequences from RNase P with RNA cleavage activity, hairpin ribozyme structures and Hepatitis Delta virus based ribozymes. The general design and optimization of ribozyme directed RNA cleavage activity is well understood in the art.

The other variable on ribozyme design is the selection of a cleavage site on a given target RNA. Ribozymes are targeted to a given sequence by virtue of annealing to a site by complimentary base pair interactions. Two stretches of homology are required for this targeting. These stretches of homologous sequences flank the catalytic ribozyme structure defined above. Each stretch of homologous sequence can vary in length from 7 to 15 nucleotides. The only requirement for defining the homologous sequences is that, on the target RNA, they are separated by a specific sequence which is the cleavage site. For hammerhead ribozyme, the cleavage site is a dinucleotide sequence on the target RNA is a uracil (U) followed by either an adenine, cytosine or uracil (A, C, or U). The frequency of this dinucleotide occurring in any given RNA is statistically 3 out of 16. Therefore, for a given target messenger RNA of 1000 bases, 187 dinucleotide cleavage sites are statistically possible.

Designing and testing ribozymes for efficient cleavage of a target RNA is a process well known to those skilled in the art. The identification of operative and preferred sequences for use in down regulating a given gene is simply a matter of preparing and testing a given sequence, and is a routinely practiced "screening" method known to those of skill in the art.

In another approach, it is also possible that genes may be introduced to produce novel transgenic plants which have reduced expression of a native gene product by the mechanism of co-suppression. It has been demonstrated in tobacco, tomato, and petunia that expression of the sense transcript of a native gene will reduce or eliminate expression of the native gene in a manner similar to that observed for antisense genes. The introduced gene may encode all or part of the targeted native protein but its translation may not be required for reduction of levels of that native protein.

In another approach, as described in more detail in the Examples herein, DNA elements including those of transposable elements such as Ds, Ac, or Mu, may be inserted into a gene to cause mutations. These DNA elements may be inserted in order to inactivate (or activate) a gene and thereby "tag" a particular trait. In this instance the transposable element does not cause instability of the tagged mutation, because the utility of the element does not depend on its ability to move in the genome. Once a desired trait is tagged, the introduced DNA sequence may be used to clone the corresponding gene, e.g., using the introduced DNA sequence as a PCR primer together with PCR gene cloning techniques (Shapiro, 1983; Dellaporta et al., 1988). Once identified, the entire gene(s) for the particular trait, including control or regulatory regions where desired, may be isolated, cloned and manipulated as desired. The utility of DNA elements introduced into an organism for purposes of gene tagging is independent of the DNA sequence and does not depend on any biological activity of the DNA sequence, i.e., transcription into RNA or translation into protein. The sole function of the DNA element is to disrupt the DNA sequence of a gene.

It is further contemplated that unexpressed DNA sequences, including novel synthetic sequences, could be introduced into cells as proprietary "labels" of those cells and plants and seeds thereof. It would not be necessary for a label DNA element to disrupt the function of a gene endogenous to the host organism, as the sole function of this DNA would be to identify the origin of the organism. For example, one could introduce a unique DNA sequence into a plant and this DNA element would identify all cells, plants, and progeny of these cells as having arisen from that labeled source. It is proposed that inclusion of label DNAs would enable one to distinguish proprietary germplasm or germplasm derived from such, from un-labelled germplasm.

The following experimental data are provided to illustrate the invention. It is to be understood that a person skilled in the art who is familiar with the methods may use other yeast strains, recombinant vectors, and methodology which can be equally used for the purpose of the present invention. These alterations are included in the scope of the invention.

III. EXAMPLES

The embodiments described here demonstrate phenotypic profiling of root architecture in combination with GWAS to identify ZmCIPK15, a novel regulatory gene controlling root angle in maize. Functional evidence for ZmCIPK15 as a regulator controlling root angle in maize was demonstrated by gene expression in relevant root tissues and predicted phenotypic changes in mutant phenotypes. Root angle changes attributed by the ZmCIPK15 gene have functional implications for soil resource capture and plant performance under edaphic stresses as predicted by functional-structural modeling and validated in the field.

We evaluated 436 diverse inbred lines from the Wisconsin Diversity (WiDiv) association panel[21,22] at anthesis for root architecture in four field environments. Using the 'shovelomics' high-throughput phenotyping method, field-grown root crowns were excavated and evaluated for root angle (FIG. 1). Results revealed 9-fold variation for brace and crown root angle in the WiDiv and root angle ranged from 10 to 90 degrees (FIGS. 1C, 1D, and 1E). Despite substantial environmental variation, broad-sense heritability ($H^2$) was high for root angle ($H^2=0.64$). Our observations suggest that considerable variation for root angle exists in maize and breeding for root angle can be carried out within Zea mays.

Genetic variation for root growth angle that improves the capture of soil resources, including nitrogen, has been observed in nodal roots in maize[23,24] sorghum[6], foxtail millet[24], and rice[25] and seminal roots in barley[26] and wheat[9,12]. Few QTL have been detected for root angle including bending angle in rice[27], basal root growth angle in common bean[28], nodal root angle in maize[29,30], and nodal root angle in sorghum[7]. Additional QTL have been detected for root system width in maize[31], deep root weight in rice[13], and ratio of deep rooting in rice[32], which could be related to root angle. Detection of root angle QTL for plants grown in the greenhouse and field[27-29,15] and identification of underlying gene expression networks[33] indicate a strong genetic component controlling root growth angle.

Figures 2A, 2B, 2C, 2D:
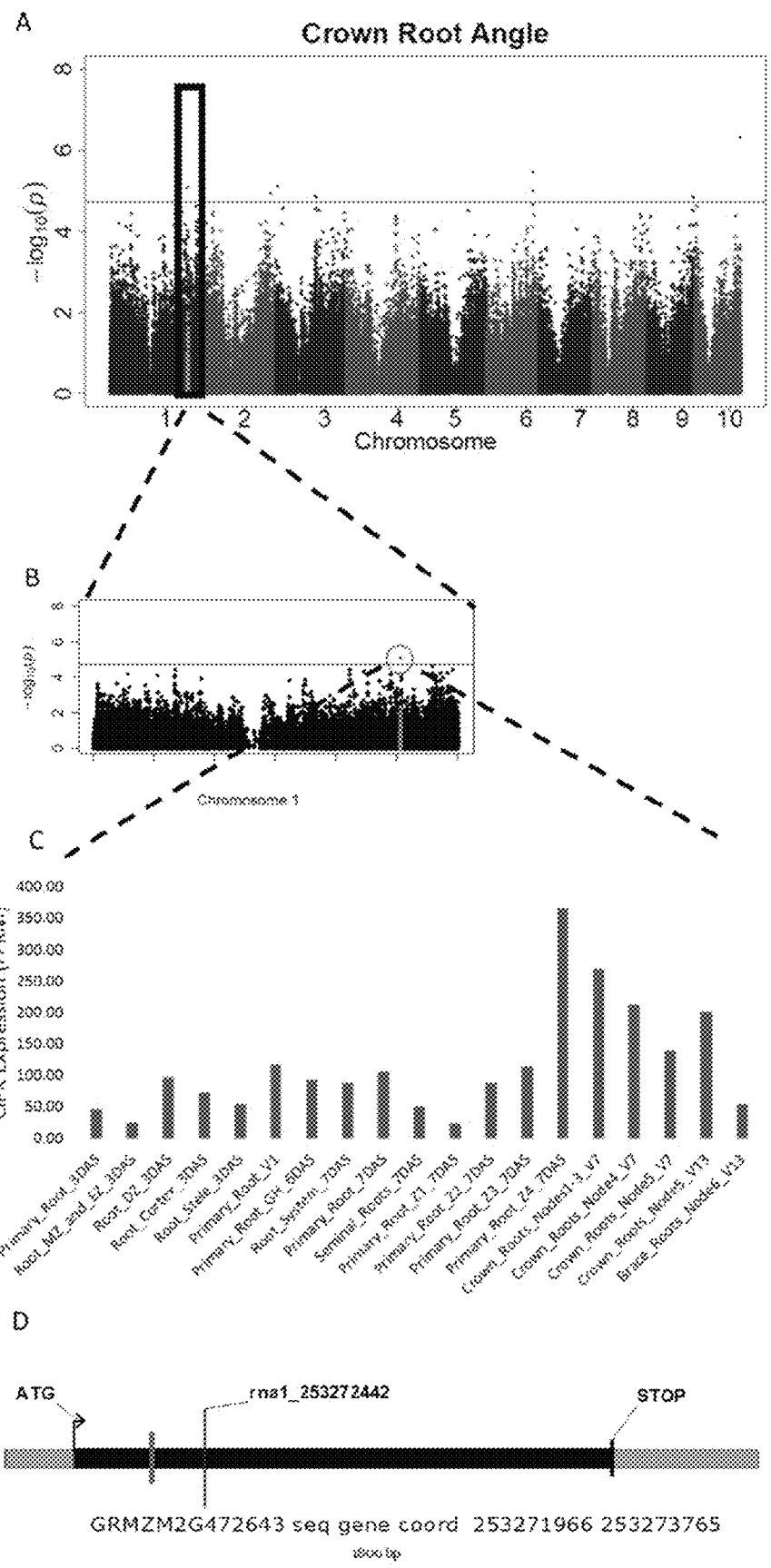
FIGS. 2A-2D show the workflow for the discovery and phenotypic validation of the mutant locus associated with root angle in maize.

To identify novel regulatory genes that control root angle, association analysis was conducted using 438,222 gene-based single nucleotide polymorphisms (SNPs)[22]. We detected six significant SNPs in the WiDiv panel for crown and brace root angle across four chromosomes at a chromosome-wide threshold level ($\alpha=0.1$). Gene model GRMZM2G472643 on chromosome one was among the most significant genes for crown root angle (FIGS. 2A and 2B). This gene encoded a member of the CBL-interacting serine/threonine-protein kinase 15 (ZmCIPK15) gene (LOC100285495) and was selected for additional analysis and prioritized based on root expression[34], its characterization in Arabidopsis[35], and known functional relationships.

Analysis of a maize gene expression atlas[34,36] revealed that the ZmCIPK15 gene is expressed in root and shoot tissues including primary, seminal, brace, and crown root classes and leaves, internodes, and seeds. Transcript abundance was elevated in the basal portion of the primary root and crown root nodes one to five at the V7 stage and node five at the V13 stage (FIG. 2C). ZmCIPK15 was not differentially expressed in different anatomical tissues. This indicates a positive regulatory function of ZmCIPK15 in crown root angle determination.

In the genome wide association study (GWAS) SNP set, 26 SNPs were located within the GRMZM2G472643 gene model (FIG. 2D). All SNPs in the gene model are present in the 20 most extreme lines for both brace root angle and crown root angle. Thirteen SNPs in the gene model were within the protein-coding region including the significant SNP and were evaluated for detrimental amino acid substitutions on protein function using a SIFT (Sorting Intolerant From Tolerant) analysis[37]. Twelve SNPs were identified to cause non-synonymous amino acid changes and one SNP was predicted to alter protein function. The significant SNP did not cause any amino acid change.

Figure 3A:
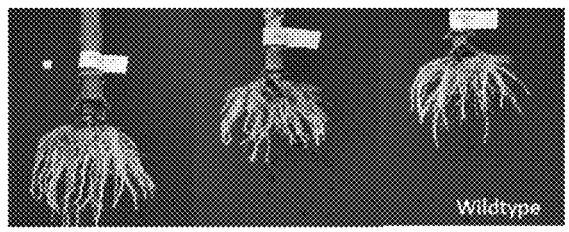
FIGS. 3A-3H show phenotypic and functional validation of the mutant locus associated with root angle in maize.
Figure 3B:
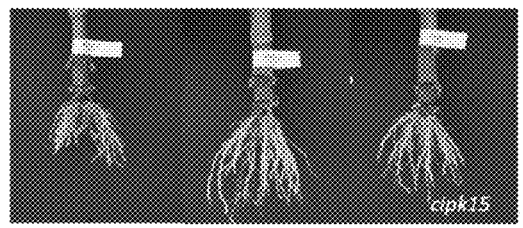
Figure 3C:
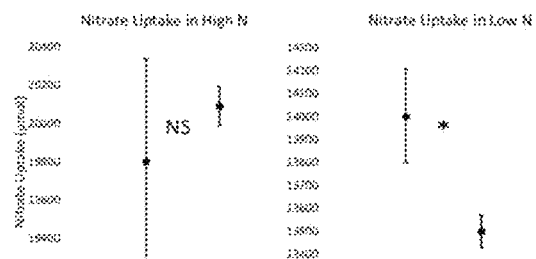
Figure 3D:
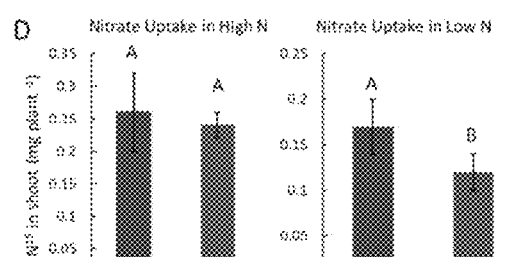
Figure 3E:
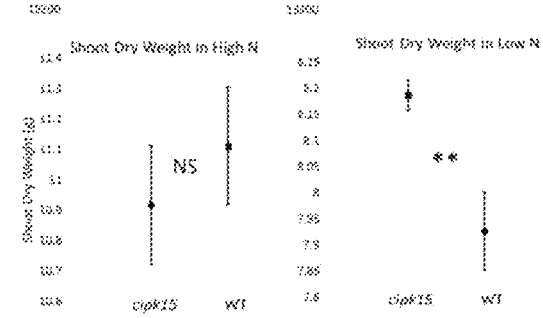
Figure 3F:
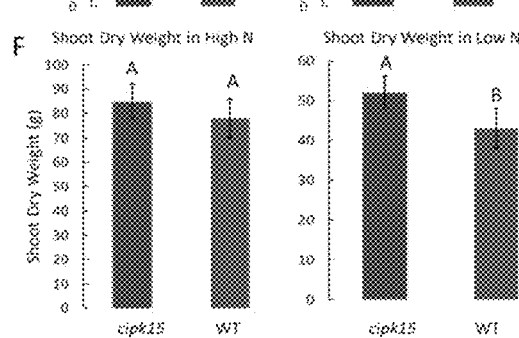
Figure 3G:
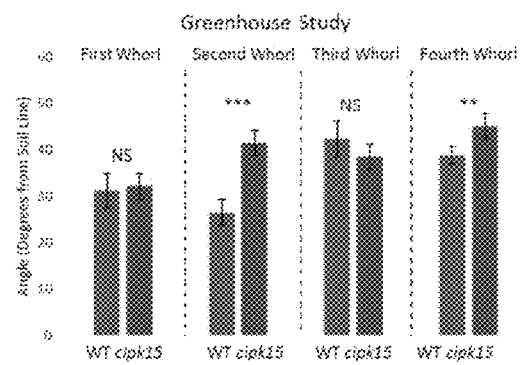
Figure 3H:
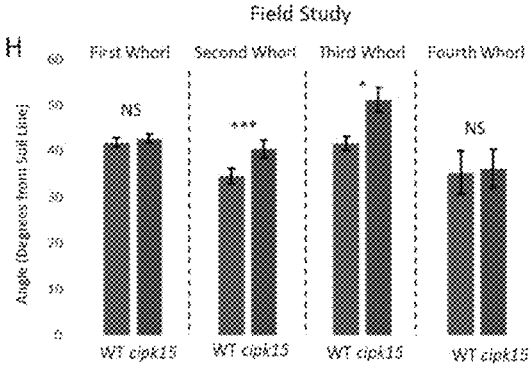

To genetically validate the role of ZmCIPK15 in root angle, we characterized a transposon-tagged mutant line harboring a Uniform Mu transposon insertion in an exon of the ZmCIPK15 gene (FIG. 2D). The mutant, mu1046464::Mu (stock: UFMu-06162) located in an exon region of the coding sequence of the GRMZM2G472643 gene, was genotyped to confirm homozygosity and phenotyped in the greenhouse and at three field sites. Homozygous mutants for the zmcipkK15 allele had a significantly steeper root angle compared to wildtype plants. Mutant root angles were on average 15 degrees steeper at node two and six degrees steeper at node four compared to the wildtype plants in the greenhouse. Mutant, field grown mature maize root systems were on average six degrees steeper at node two and nine degrees steeper at node three compared to wildtype plants (FIGS. 3A, 3G, and 3H). These results support that the hypothesis that ZmCIPK15 functions as a positive regulator of root angle in maize.

To determine the functional implications of these changes in root angle we performed SimRoot simulations to evaluate in silico plant performance and nutrient uptake with the altered root angles of the zmcipk15 mutants. Simulations demonstrated that mutant zmcipk15 phenotype resulted in significantly greater shoot dry weight and nitrate capture in low nitrogen soils, compared to wildtype plants. In high nitrogen conditions, mutant and wildtype plants had no significant differences in shoot dry weight or nitrate capture (FIGS. 3C and 3E). The ability of steeper roots to capture N in deep soil layers was verified by deep injection of $^{15}NO_3^-$. The mutant zmcipk15 had 29% greater nitrogen uptake and 17% greater shoot biomass in low N environments compared to the wildtype (FIGS. 3D and 3F).

Materials and Methods

Plant Materials and Growth Conditions—

Root angle was scored on 436 lines of the Wisconsin Diversity Panel (WiDiv)[21]. All experiments were conducted at the Ukulima Root Biology Center (URBC) in Alma, Limpopo, South Africa (24° 33_00.12S, 28° 07_25.84E, 1235 masl) under non-stress conditions on a Clovelly loamy sand (Typic Ustipsamment). Experiments were conducted during January to April of 2010, 2011, and 2012 and during November to February of 2013 in two replications in a randomized complete block design in each year. Each maize line was planted in a single row plot consisting of 20 plants per plot and row width was 75 cm and distance within a row was 23 cm. In all trials, soil nutrient levels were adjusted to meet the requirements for maize production as determined by soil tests at the beginning of the growing seasons and pest control was implemented when required. Trials were irrigated using a center pivot system.

Root Sampling—

Roots were sampled using the 'shovelomics'[41] method at anthesis. Three representative plants were selected based on height, presence of bordering plants, and general appearance for excavation in each plot. Root crowns were collected by carefully removing a soil monolith (30 cm in diameter by 15 cm deep centered on the stem) containing the intact root crown (FIG. 1A). A large portion of the soil was removed from the roots by careful shaking and the remaining soil was removed by soaking the roots in diluted commercial detergent followed by vigorously rinsing at low pressure with water. Cleaned root crowns were scored for root architecture traits. Root angle was scored on crown and brace roots as the average degrees from horizontal measured from 8 cm from the base of the stem (FIG. 1B).

Statistical Analysis—

Statistical analyses were performed using R version 2.15.1[42]. Variation within each trait and among years and replications was assessed using two-way analysis of variance. Broad-sense heritability on an entry mean basis was calculated[43]. Spearman and Pearson correlations between years and replications suggested data could be combined using best linear unbiased predictors (BLUPs). BLUPs across all years were calculated and used for subsequent analysis. Residuals were transformed according to the box cox analysis.

Genome-Wide Association Analysis—

GWAS analysis was conducted using the mixed linear Q+K model[44] (MLM) implemented in the Genomic Association and Prediction Integrated Tool (GAPIT) R package[45] using 438,222 RNA-seq based SNP markers[21,22]. The kinship matrix estimation and the principal component (PC) analysis were performed with the GAPIT package. The kinship matrix was estimated with a random set of SNPs according to the VanRaden method. The optimum number of PCs/Covariates to include for each phenotype was determine by forward model selection using the Bayesian information criterion (BIC). Quality of the GWAS model fit was evaluated with QQ plots (FIG. 1G). SNP significance is determined at a genome-wide and chromosome-wide level through the simpleM method[46]. Allelic effects are estimated relative to the minor allele. Spatial and temporal expression patterns of gene models associated with significant SNPs were evaluated using a comprehensive atlas of global transcription profiles across developmental stages and plant organs database[34,36].

Mutant Lines—

The zmcipk15 mutant allele stock (mu1046464::Mu, stock ID: UFMu-06162) was obtained from the Maize Genetics Stock Center-Uniform Mu collection. Seeds from the Stock center were grown at West Madison Agricultural Research Station, WI, USA (Latitude: 43° 03'37"N; Longitude: 89°31'54"W) during the summer of 2014 and genotyped for the transposon insertion. The CTAB method was used to isolate DNA and all primers were designed by Primer 3 based on the B73 reference sequence. Plants possessing the mutant allele were identified by genotyping using an outward facing primer in the TIR of the Mutator transposon, TIR6 (5'-AGAGAAGCCAACGCCAWCG-CCTCYATTTCGTC-3'; SEQ ID NO:3) and the ZmCIPK15 gene specific primer ZmCIPK15 F1 (5'-TTGGCACCAC-CAAGGCGCACCCTGTA-3'; SEQ ID NO:4). The wildtype (W22) allele was identified by using the gene-specific primer set ZmCIPK15 F1 and ZmCIPK15 R1 (5'-CGTCCGCCTTGGCGCCGTCGT-3'; SEQ ID NO:5). PCR conditions were 95° C. for 30 s, 63° C. for 30 s, 72° C. for 45 s, repeated for 30 cycles. Homozygous mutants and wildtype control plants (W22) were grown in six replications in control conditions at West Madison Agricultural Research Station during the summer of 2015, in four replications in high and low nitrogen environments at the Russel E. Larson Agricultural Research Station, PA, USA (Latitude: 40° 42'35"N; Longitude: 77° 56' 59"W) in 2016 and 2017, and in four replications in water-stress and well-watered environments at the Apache Root Biology Center, AZ, USA (Latitude: 32° 01'57"N; Longitude: 109° 41'30"W) in 2016. Root crowns were excavated using shovelomics, and phenotyped for root angle. Root crowns were imaged based on an intensive method, imaging root angle at every whorl[47]. Root angle was phenotyped at a soil depth of 8 cm.

The ability of steeper roots to capture N in deep soil layers was studied by deep injection of $^{15}NO_3^-$ at the Russel E. Larson Experimental Station in 2016 and 2017. A soil auger was used to excavate a cylinder of soil to a depth of 50 cm adjacent to three representative plants per plot. PVC pipes with a length of 75 cm and a diameter of 5 cm were inserted into the hole and 5 mL of $K^{15}NO_3^-$ solution (0.46 mg $^{15}N$ $mL^{-1}$, 98% $^{15}N$ enriched) was injected into each hole. Following injection, each hole was filled with field soil. Seven days after $^{15}NO_3^-$ injection, the shoot biomass of the adjacent plant was harvested for $^{15}N$ analysis.

Greenhouse experiments were conducted in a greenhouse at University Park, Pa., USA (40° 4'N 77°49'W) under constant conditions (14/10 h day/night: 28/26° C. day/night: 40-70% relative humidity). Ten wildtype and ten mutant plants were grown. Plants were grown in pots 50 cm in height by 27 cm top diameter and 21 cm bottom diameter with a total volume of 20 L. The growth medium consisted of (by volume) 50% commercial grade sand (Quikrete Companies Inc. Harrisburg, Pa., USA), 35% vermiculite (Whittemore Companies Inc., Lawrence, Mass., USA), 5% Perlite (Whittemore Companies Inc., Harrisburg, Pa., USA), and 10% topsoil (Hagerstown silt loam top soil (fine, mixed, mesic Typic Hapludalf)). Mineral nutrients were provided by mixing the media with 50 g of OSMOCOTE PLUS fertilizer consisting of (in %); N (15), P (9), K (12), S (2.3), B (0.02) Cu (0.05), Fe (0.68), Mn (0.06), Mo (0.02), and Zn (0.05) (Scotts-Sierra Horticultural Products Company, Marysville, Ohio, USA) for each column. Zinc/micros foliar spray was used as needed. The seeds were surface sterilized in 25% commercial bleach for 3 min. and coated with Captan fungicide (0.2 g $L^{-1}$) for 10 to 30 minutes. Seeds were imbibed in 0.5 mM $CaSO_4$ and germinated by placing them in a dark chamber at 30±1° C. for three days prior to transplanting. Wildtype and mutant plants were grown in ten replications. At harvest (i.e., 40 days after planting), plants were carefully removed from pots, root crowns were washed with low pressure water, and photographed at every whorl for angle phenotyping using the protocol previously described.

SimRoot Simulations—

The Functional Structural Plant Model, SimRoot[48,49] was used to test the differences in performance in wild type and mutant maize genotypes. Root system is simulated from germination to 40 days after germination. Carbon availability for growth is determined initially by seed reserves and later by photosynthesis. Available carbon is allocated between different root classes with axial roots having a higher priority over lateral roots. SimRoot coupled with SWMS-3D was used to simulate nitrate uptake[48,50]. Nitrate was allowed to leach to deeper soil strata over time following precipitation events. A stress factor is used to reduce the photosynthetic efficiency for plants under nitrogen stress. This results in reduced carbon availability which results in reduced root length of different root classes affecting nutrient uptake. The number of nodal roots, initial root growth angle and the lateral root branching density was specified based on empirical data. The plants were simulated for 40 days in environments with low, medium high and high nitrate (30 kg/ha, 106 kg/ha and 213 kg/ha respectively) and the biomass accumulated as well as nitrate uptake obtained.

REFERENCES

1. Lynch, J. P. Root phenes for enhanced soil exploration and phosphorus acquisition: tools for future crops. *Plant Physiol.* 156, 1041-9 (2011).
2. Lynch, J. P. Steep, cheap and deep: an ideotype to optimize water and N acquisition by maize root systems. *Ann. Bot.* 112, 347-57 (2013).
3. Trachsel, S., Kaeppler, S. M., Brown, K. M. & Lynch, J. P. Maize root growth angles become steeper under low N conditions. F. *Crop. Res.* 140, 18-31 (2013).

4. Lynch, J. P. & Brown, K. M. New roots for agriculture: exploiting the root phenome. *Philos. Trans. R. Soc. Ser. B* 367, 1598-604 (2012).
5. Hammer, G. L. et al. Can changes in canopy and/or root system architecture explain historical maize yield trends in the U.S. corn belt? *Crop Sci.* 49, 299 (2009).
6. Tsuji Wataru et al. Development and distribution of root systems in two grain sorghum cultivars originated from Sudan under drought stress. *Plant Prod. Sci.* 8, 553-562 (2005).
7. Mace, E. S. et al. QTL for nodal root angle in sorghum (*Sorghum bicolor* L. Moench) co-locate with QTL for traits associated with drought adaptation. *Theor. Appl. Genet.* 124, 97-109 (2012).
8. Bonser, A., Lynch, J. & Snapp, S. Effect of phosphorus deficiency on growth angle of basal roots in *Phaseolus vulgaris*. *New Phytol.* 132, 281-8 (1996).
9. Oyanagi, A. Gravitropic response growth angle and vertical distribution of roots of wheat (*Triticum aestivum* L.). *Plant Soil* 165, 323-326 (1994).
10. Zhu, J., Kaeppler, S. M. & Lynch, J. P. Topsoil foraging and phosphorus acquisition efficiency in maize (*Zea mays*). *Funct. Plant Biol.* 32, 749 (2005).
11. Liao, H. et al. Effect of phosphorus availability on basal root shallowness in common bean. *Plant Soil* 232, 69-79 (2001).
12. Manschadi, A. M., Hammer, G. L., Christopher, J. T. & DeVoil, P. Genotypic variation in seedling root architectural traits and implications for drought adaptation in wheat (*Triticum aestivum* L.). *Plant Soil* 303, 115-129 (2008).
13. Shen, L., Courtois, B., McNally, K. L., Robin, S. & Li, Z. Evaluation of near-isogenic lines of rice introgressed with QTLs for root depth through marker-aided selection. *Theor. Appl. Genet.* 103, 75-83 (2001).
14. Oyanagi, A., Nakamoto, T. & Morita, S. The gravitropic response of roots and the shaping of the root system in cereal plants. *Environ. Exp. Bot.* 33, 141-158 (1993).
15. Uga, Y. et al. Control of root system architecture by DEEPER ROOTING 1 increases rice yield under drought conditions. *Nat. Genet.* 45, 1097-1102 (2013).
16. Zhu, J., Mickelson, S. M., Kaeppler, S. M. & Lynch, J. P. Detection of quantitative trait loci for seminal root traits in maize (*Zea mays* L.) seedlings grown under differential phosphorus levels. *Theor. Appl. Genet.* 113, 1-10 (2006).
17. Zhu, J., Kaeppler, S. M. & Lynch, J. P. Mapping of QTLs for lateral root branching and length in maize (*Zea mays* L.) under differential phosphorus supply. *Theor. Appl. Genet.* 111, 688-95 (2005).
18. Hund, A. et al. QTL controlling root and shoot traits of maize seedlings under cold stress. *Theor. Appl. Genet.* 109, 618-29 (2004).
19. Zhu, J., Ingram, P. A., Benfey, P. N. & Elich, T. From lab to field, new approaches to phenotyping root system architecture. *Curr. Opin. Plant Biol.* 14, 310-7 (2011).
20. Hochholdinger, F., Park, W. J. & Feix, G. H. Cooperative action of SLR1 and SLR2 is required for lateral root-specific cell elongation in maize. *Plant Physiol.* 125, 1529-1539 (2001).
21. Hansey, C. N., Johnson, J. M., Sekhon, R. S., Kaeppler, S. M. & Leon, N. De. Genetic diversity of a maize association population with restricted phenology. *Crop Sci.* 51, 704 (2011).
22. Hirsch, C. N. et al. Insights into the maize pan-genome and pan-transcriptome. *Plant Cell* 26, 121-35 (2014).
23. Bayuelo-Jiménez, J. S. et al. Genotypic variation for root traits of maize (*Zea mays* L.) from the Purhepecha Plateau under contrasting phosphorus availability. *F. Crop. Res.* 121, 350-362 (2011).
24. Nakamoto, T., Shimoda, K. & Matsuzaki, A. Elongation angle of nodal roots and its possible relation to spatial root distribution in maize and foxtail millet. *Japanese J. Crop Sci.* 60, 543-549 (1991).
25. Kato, Y., Abe, J., Kamoshita, A. & Yamagishi, J. Genotypic variation in root growth angle in rice (*Oryza sativa* L.) and its association with deep root development in upland fields with different water regimes. *Plant Soil* 287, 117-129 (2006).
26. Hargreaves, C. E., Gregory, P. J. & Bengough, A. G. Measuring root traits in barley (*Hordeum vulgare* ssp. *vulgare* and ssp. *spontaneum*) seedlings using gel chambers, soil sacs and X-ray microtomography. *Plant Soil* 316, 285-297 (2008).
27. Norton, G. J. & Price, A. H. Mapping of quantitative trait loci for seminal root morphology and gravitropic response in rice. Euphytica 166, 229-237 (2009).
28. Liao, H. et al. Genetic mapping of basal root gravitropism and phosphorus acquisition efficiency in common bean. *Funct. Plant Biol.* 31, 959-970 (2004).
29. Omori, F. & Mano, Y. QTL mapping of root angle in F2 populations from maize B73×teosinte *Zea luxurians*. *Plant Root* 1, 57-65 (2007).
30. Guingo, E., Yannick, H. & Charcosset, A. Genetic analysis of root traits in maize. *Agronomie* 18, 225-35 (1998).
31. Burton, A. L. et al. QTL mapping and phenotypic variation for root architectural traits in maize (*Zea mays* L.). *Theor. Appl. Genet.* 2293-2311 (2014). doi:10.1007/s00122-014-2353-4
32. Uga, Y. et al. A major QTL controlling deep rooting on rice chromosome 4. *Sci. Rep.* 3, 3040 (2013).
33. Vidal, E. A., Tamayo, K. P. & Gutierrez, R. A. Gene networks for nitrogen sensing, signaling, and response in *Arabidopsis thaliana*. *Wiley Interdiscip. Rev. Syst. Biol. Med.* 2, 683-93 (2010).
34. Stelpflug, S. C. et al. An expanded maize gene expression atlas based on RNA-sequencing and its use to explore root development. *Plant Genome* 314-362 (2015). doi:10.3835/plantgenome2015.04.0025
35. Kolukisaoglu, U., Weinl, S., Blazevic, D., Batistic, 0. & Kudla, J. Calcium sensors and their interacting protein kinases: Genomics of the *arabidopsis* and rice CBL-CIPK signaling networks. *Genome Anal.* 134, 43-58 (2014).
36. Sekhon, R. S. et al. Genome-wide atlas of transcription during maize development. *Plant J.* 66, 553-563 (2011).
37. Kumar, P., Henikoff, S. & Ng, P. C. Predicting the effects of coding non-synonymous variants on protein function using the SIFT algorithm. *Nat. Protoc.* 4, 1073-1081 (2009).
38. Jung, J. K. H. & McCouch, S. Getting to the roots of it: Genetic and hormonal control of root architecture. *Front. Plant Sci.* 4, 186 (2013).
39. Wasson, A. P. et al. Traits and selection strategies to improve root systems and water uptake in water-limited wheat crops. *J. Exp. Bot.* 63, 3485-3498 (2012).
40. Tuberosa, R. et al. Searching for quantitative trait loci controlling root traits in maize: a critical appraisal. *Plant Soil* 35-54 (2003).
41. Trachsel, S., Kaeppler, S. M., Brown, K. M. & Lynch, J. P. Shovelomics: high throughput phenotyping of maize (*Zea mays* L.) root architecture in the field. *Plant Soil* 341, 75-87 (2011).

42. R Core Team. R: A Language and Environment for Statistical Computing. (2014). at <http://www.r-project.org>
43. Fehr, W. *Principles of Cultivar Development.* (Macmillan Publishing Company, 1993).
44. Zhang, Z. et al. Mixed linear model approach adapted for genome-wide association studies. *Nat. Genet.* 42, 355-60 (2010).
45. Lipka, A. E. et al. GAPIT: genome association and prediction integrated tool. *Bioinformatics* 28, 2397-9 (2012).
46. Gao, X., Starmer, J. & Martin, E. R. A multiple testing correction method for genetic association studies using correlated single nucleotide polymorphisms. *Genet. Epidemiol.* 32, 361-9 (2008).
47. York, L. M. & Lynch, J. P. Intensive field phenotyping of maize (*Zea mays* L.) root crowns identifies phenes and phene integration associated with plant growth and nitrogen acquisition. *J. Exp. Bot.* 66, 5493-5505 (2015).
48. Postma, J. a, Dathe, A. & Lynch, J. The optimal lateral root branching density for maize depends on nitrogen and phosphorus availability. *Plant Physiol.* (2014). doi: 10.1104/pp. 113.233916
49. Lynch, J. P., Nielsen, K. L., Davis, R. D. & Jablokow, A. G. SimRoot: Modellig and visualization of root systems. *Plant Soil* 188, 139-151 (1997).
50. Postma, J. A. & Lynch, J. P. Root cortical aerenchyma enhances the growth of maize on soils with suboptimal availability of nitrogen, phosphorus, and potassium. *Plant Physiol.* 156, 1190-201 (2011).

As can be appreciated, the results described in the above examples support the utility of the materials and methods described and claimed herein. Other embodiments and uses of the invention will be apparent to those skilled in the art from consideration from the specification and practice of the invention disclosed herein. All references cited herein for any reason, including all journal citations and U.S./foreign patents and patent applications, are specifically and entirely incorporated herein by reference. It is understood that the invention is not confined to the specific materials, methods, formulations, reaction/assay conditions, etc., herein illustrated and described, but embraces such modified forms thereof as come within the scope of the following claims.

The invention claimed is:

1. A method of increasing nutrient or water deficient abiotic stress tolerance in a maize plant, comprising introducing in a maize plant a targeted non-natural mutation in maize gene $ZmCIPK_{15}$, wherein the mutation decreases the expression of maize gene $ZmCIPK_{15}$ relative to a control maize plant of the same variety lacking the non-natural mutation, wherein said maize plant exhibits increased nutrient or water deficient abiotic stress tolerance relative to a control maize plant of the same variety lacking said non-natural mutation, and wherein the non-natural mutation is not a transposon insertion mutation.

2. A method of increasing root angle in a maize plant, comprising introducing in a maize plant a targeted non-natural mutation in maize gene $ZmCIPK_{15}$, wherein the mutation decreases the expression of maize gene $ZmCIPK_{15}$ relative to a control maize plant of the same variety lacking the non-natural mutation, wherein said maize plant exhibits increased root angle relative to a control maize plant of the same variety lacking said non-natural mutation, and wherein the non-natural mutation is not a transposon insertion mutation.

3. The method of claim 1, wherein the maize is a maize hybrid or corn-belt dent maize germplasm.

4. The method of claim 1, wherein the non-natural mutation is within the promoter region of the $ZmCIPK_{15}$ gene.

5. The method of claim 1, wherein the non-natural mutation is a deletion of the $ZmCIPK_{15}$ gene that results in complete loss of function of $ZmCIPK_{15}$.

6. The method of claim 1, wherein the non-natural mutation is a CRISPR-Cas9 mediated knockout of the gene.

7. The method of claim 1, wherein the maize is a maize inbred line.

8. The method of claim 1, wherein the increase in abiotic stress tolerance is an increase is tolerance to drought or low nitrogen conditions.

9. The method of claim 1, wherein the maize plant has an increase in root angle of at least 2 degrees relative to a maize plant of the same variety lacking the non-natural mutation.

10. The method of claim 2, wherein the maize is a maize hybrid or corn-belt dent maize germplasm.

11. The method of claim 2, wherein the non-natural mutation in within the promoter region of the $ZmCIPK_{15}$ gene.

12. The method of claim 2, wherein the non-natural mutation is a deletion of the $ZmCIPK_{15}$ gene that results in complete loss of function of $ZmCIPK_{15}$.

13. The method of claim 2, wherein the non-natural mutation is a CRISPR-Cas9 mediated knockout of the gene.

14. The method of claim 2, wherein the maize is a maize inbred line.

15. The method of claim 2, wherein the maize plant has an increase in root angle of at least 2 degrees relative to a maize plant of the same variety lacking the non-natural mutation.

16. The method of claim 15, wherein the maize plant has an increase in root angle of at least 5 degrees relative to a maize plant of the same variety lacking the non-natural mutation.

* * * * *

SEQUENCE LISTING

<160> NUMBER OF SEQ ID NOS: 5

<210> SEQ ID NO 1
<211> LENGTH: 1290
<212> TYPE: DNA
<213> ORGANISM: Zea mays B73

<400> SEQUENCE: 1

```
atggccaaga gcaagtcgtc cgccaaggcc ggccccccgc tcctcggcaa gtacgagctc      60
ggccacctcc tcggccgggg caacttcgcc aaggtatacc acgcgcgctg tctcggcgga     120
ggcgaccccg tggccgtgaa ggtgctggac aaggccgggt tggccgccac gggcatggcg     180
tcgcgtctcc tgcgcgaggt gtccgccatg cgccgcctga gccacccaa cgtgctccgc      240 ctccacgagg tgctggcgac gcgctccaag gtgtacctcg tgatggagct ggccccgggc     300
ggggacctcc tgacccggct ggcgtcgctg ccgtcgcgca ggctccccga gcacgcggcg     360
cggcgcgtgt tcctccagct ggcgtcggcg ctcatctaca gccacgcgcg cggggtgttc     420
caccgcgacg tgaagccgca gaacgtgctg ctggacgccg agggcaacct caaggtgtcc     480
gacttcggcc tcgcggcgct cccggactcg gtccgcgacg acgggcgcct gcacacggcg     540
tgcggcaccc cggcgttcgc ggcgcccgag gtgctccggc gcagggccta cgacggcgcc     600
aaggcggacg cgtggtcctg cggggtcatc ctcttcgtcc tcctcgcggg ccacctcccc     660
ttcgacgacg ccaacatcgc cgacatgtgc cgcagggcgc accgccggga gtacacggtc     720
ccgcggtggg tgtcgcagcc ggcgcgccgc ctcgtggcgc gcctgctgga cccgaacccg     780
gcgacgcgcc tcgccgtcgc ggagctcgcc ggccacccct ggttcaagcg ctcgctcagc     840
gtggactccc agctcggcgg cctcctggac ggccaggcgg agcgcgagct ggcgttccag     900
gccccgccgg cgttgaacgc cttcgacatc atctccatgt ccccccgggct ggacctgtcg     960 ggcctgttcg gcgagggcag gcgccgccgc gagaagcggt tcatgacgac ggcgtccccg    1020
gagcgggcgg tggagcggct cgcgcaggcc ggcgcgaggc tcggctactt cattgtgggg    1080
aagaaggggg ccgagcgcct gccgctgggc gtcctgccgg gcctcgtggc catgtcgatg    1140
gagatgtcgg aggtgtcgcc ggagctgatg ctggtggagc tgaggctgga gggcggccac    1200
```

```
ggcgacgagg acgaggcgtt cgggtgggag gagctccggg ttgagctggg ggacgtggta    1260
acagcatggc acgtgagtga agaaggttaa                                    1290

<210> SEQ ID NO 2
<211> LENGTH: 13290
<212> TYPE: DNA
<213> ORGANISM: Zea mays B73

<400> SEQUENCE: 2
cactttcgga cttgtccatt gaaattgatc ccataaaccc tagtttacta attcaaatga     60
aatatgtgtg tgtatgtgtg aaggatctct atgcggtacg caactggttt tgtatatata    120
tggcagcact tacatgttta atacttgca atatgtgaat atcatagaag aacagctaaa     180
gtaaaatatg agcgcacagt aagattttct agtatacaca aattaagtaa ctttatcagc    240
tgtacttttt aagtttatat ttctactgac gattaaacta tataaaaggc cagtacaaaa    300
atttatagat gttcatgttc ttagcaacca cgcacgattt ttggcttttt cttttaactt    360
ctgattttga aggtcagaat tctatatgtg catatattcg cgtaccaata cttcatgtgc    420
accggttatt atctctaata ccttagcata ttgctggttc attagtataa gcaaactagc    480
tagactggat ctgctgtgca cactactata acagttcaga cttttataga taggcactac    540
tattcctctt ccatgaggag actactcgat cggataaata atctacgctc agttaagata    600
aggccctgtt tgtttcaact tatagattat ataatctata ttataattta gattatataa    660
tctggattat ttgctctgga ttaaataagc taggtgctac tgtttgttag ctcagattat    720
ttggactcgg cttattattc atatgcatac aaatacaata ataccttga ttgttttaat     780 tgtctggtgg gtgagaacgc ttatagatag gtggatgaca attggaagta attttaatca    840
acttgccatg ggtagtgggt ctttcataaa aaataagctg aaataagcac cctttgatga    900
gcttatagga ttatcataat ctcaagtgct agattatata atcttatcag ataagttgtt    960
tgtttgtttc ctcactagct tatttacatt ggattatata atctatatag attataatct   1020
caaacaaaca tggcctaagt tggcataaat cgattatcta ctaataggca aagttttttcc   1080 tggtgcagca gaccgactgt gcatgcatgt tttgaaacta acgcaaacac gtacagtcgt   1140
acactggttc ggtcgaaccg aaagcagaga cttgcttttt ttagttgatt tactactctt   1200
ggtccaaaag gaatatgtgc gttcaactct ttgaattgat cgaaacgaat taattagtat   1260
cccctaacta tgaaaataat atgaccgaga taattttggt tgaaatgcaa gatgccatac   1320
acatatgcct gtgaaatgct agctggagtt caaaagcaga ttgcgacgcg caaaaaaagg   1380
acacacaaca agaggatgat ttacttcact ttgaagtgaa gtctctcaaa gcggagagaa   1440
gaagatatac atgcacacta gccaacgcag cattgatcca tatagatata tagtagcgct   1500
cgaatcgaac tagagaatag cgatgttgaa actagacctg gcaaaaatat ctatcgtctc   1560
ccacatgcat cgtcaattaa ttttaggtgg tgtttgattg cactagaact aatagttaat   1620
taatagttaa tgattacatt aaaaacgtcc tagctaatgg ttcaactatt aactattttt   1680
ttttgtaaat tagttaataa taagctagtt attttgttagc taactaattt cattagtaat   1740
ttttagtcga ctaataattc aaaatgaggt ggtgcatcac tggttcattt atcaagtttg   1800
gtggaatgat ctcatttctc atattagtat taaccaacta agagcaatga ggtggactta   1860
tttcattcca caaccaaac gaaaaaagtg agaagtgaga agatgatatg gactagctcg    1920
ttccttaaaa caaacaccct ataaatatcg aattcatcgt ttagattaat gttttttttaa   1980 actatatata taaatactcc tgtggagagc atgggttcat ttgtttgcaa tacatgcatt   2040
```

```
atgcatagtg gggttagatg ggcgaatgcg attcgatcgt ttgattagtc tcaggctctc    2100
tcatatgtag cagctagtgc gagatcttct ggctgtgtta ctttgcatgt cacatgttca    2160
tggttcagtt cgccctttcc ggtatcccaa aggttacttg cactgcgcta gctgctgttg    2220
tttaagactt tgcatgaaac aagtgcatcc ttcgttttag aaaagaaaaa ctaattaaaa    2280
taaaaggctg tatctccagt atgatcggca caggtgaaaa gcttcggctt tcagcgcgta    2340
ttttggacga acgtgtagat ttgcatctcc ttgacgagaa gcttgcacta gcccaaagct    2400
tgcacttgcg catgttcgag agagaaaaaa aatccgatcc gtgtatagat ctctttctgg    2460
aggaggtgtg tcgttggaa taatatatat atcttctaca aataaaaggc ctctcgcaca    2520
ttattttctg tttacacaag tttgtaaaag gttcctcatg aacatttata catgcttaaa    2580
caagctaata aacacggtgt ttttctcccc cttttttcc ccaggattct ttggagatag    2640
gggcctttgg agattagaaa aaacatctag agcgtcgtcg tcggcaccga tgcaatgagg    2700
gtctctgctt cctctttgat tcatacgcag aaagtgtttc atgctcctct gtatatgttg    2760
aaagtattgt tgataaggct cattcttaat gcggtgtgct cttttttttt taaaaaaaga    2820
atagattaga tcatgtaaaa ttttgtata gaaaataata ttttatggtt gagtgggta    2880 tatgtagata atttagggt aaccactgcg gggaaaacaa aagtaggggg tagaatctgg    2940
acaggctggg atctaggaat ctcccgtccc cgctcatgca tccaatcagt gaaaagcgg    3000 catgcattgt accgcacgtg tctgtgcata caaccaatca ggggtttgca cgcatgcgga    3060
ggacatggac gcgggtagca gggaaaccaa tcatgcgaaa taggtttttg caggtgcatg    3120
tgcgtatata accacccgcg cgcaggagta gggatgcgta taatagatag aatgatgaag    3180
atatatctgc gtaggctcgg tgatgtttgt acgatggatg aattgaaggc ggcatttccc    3240
acttgcctgc gctacgtacc gacggtgtgc tgcggggcga ctggcgagaa ggaaggggac    3300
agacacgcac ggcatgtcgg catccagctg ctggtgcgca cccaacgcag gcaaccgacg    3360
gaggaaaaac gaaaaggaa accagccagg ctcgcgacgc tgctgctgct gctgggcggg    3420
cgctctgcta gccgttggtt ggcacgacag ataatgatag atggatccaa tccaacgcac    3480 cacccgtcc gtgtcacgac ggcggatcgg aagccagaaa gcaaggggct gctgctggct    3540
ctggctggtc catcagtcat cacgtatacg cgtatcgacc agccgcctat gcgcgcgcag    3600
gcagtgcaag aatgaacgaa cgttcccaag tgcaggtgac ccgtgaccgt aggcgtgaac    3660
caccggtcta actagtcaag tactagctac caggtagttt gccatatgta tctgagatag    3720
tgtatggcgc ccgaggcgag acgttttat ctacgtactg tactccacac ttggcgctat    3780
cctggatgtt cctgttgccg ccggggacgg gaacaacacc gtagcgccta gcgcgggtgc    3840
gggcgcgggt ggtgacatct gatgtacgcc accgggctcc ggagcgcgac ggccaggcag    3900
ccccggcgcc acacgcggcg cgctagctag atttttcttc cccgaaaaag ctggacgggg    3960
acctcgccct cgccgcgctg gttccgttcc gttccgcccc gcggatattt tgcgtggagc    4020
ctccccaccc cgcggcgacc ccagcgggca gcggctcctt tccgcgtccg ccgccgcacc    4080
cgcgtctcgg tctacggtct ctcgtcacgt ctcgctctcg cacctcacct gcgcacggcg    4140
ccaccacagg atgctctgtc tccctctctc ccactcccag cttttgtgag gccagagcaa    4200
cgtccaggaa cctctggtgc gtgggagaat cggacgccgc gtcctgcctc tcccaagctc    4260
caaagggcgg gcacttgaca cgtactggca gtaggctctc tacccgatca tcagaaacgc    4320
cagcaaacag atcagctccc ccgcgccgcg ctgcgctgga gagctggagg aggagagcaa    4380
```

```
gagaaaaaaa aaatctcagg ttccgcccgc cgtggcaact ggcaaccgag ttccttgtcc    4440
tttttccgag ttcgtgttga actcaattct cagagcctgg ttcacacgct tgaagatagt    4500
atcttacaca attctacctt gcaaaaaatg tttaagggtt agtttgggac ataattttct    4560
taagatttgt ttatttttcc aaaagaaatt agctcatttt tctgggtaaa atagaaaatt    4620
tcttaaaaaa atggagttca caaattagcc ctaaatattc agggatttcc acatctgtta    4680
cataactccc atagcatcgc tacaaatttc agaggaaaaa aggagaccat gtccatgtat    4740
cttctccaaa aacaaccatt aaagttcaga ggaaaaaagg aggagatttt ttttttcttt    4800
tttggcgagg aggggggaac aaaaagaaat atcgtcttgt gagctgctgg ccttggtatt    4860
aaaaatctgg agaccatgaa tattggcctt ctgtgcaagt ggtggtggaa aatatccaaa    4920
actctgactc ccccatccgg gaaaaattga ctaaggtgag ggattatttt ttttagataa    4980
tgtaggtaag gaattattat cttaagggca tgatcattgt tactaaatcc ggatacaaaa    5040
ctgccttctc gactgataat tggctagata gggagcccat gaacattact cacccagatc    5100
tttatgaaat atgtgatgaa aaaggatatc tcggttaaga atgccaaaga agaaaaaaaa    5160
ctagcagcta aaattcacaa tgttgatgaa ttatgactta tgagaatcaa ttaactggga    5220
taacctcttt acggagttca aagatacttc tcaacctttt catgtcttgg ttcaaatata    5280
aaccttccaa atacaataag gccttgtttg tttactctat agactatgta atccagttta    5340
attaagttaa aagacaaaca aacaacatat attattaggt ggattataca atctatagct    5400
agattatgat aattcataag cagatcatta tataattcat aagctagatt atatattcgg    5460
gaagaaaaca agcagggttt aagagtgtgt ttgtttggga ttataatctg cctagattat    5520
ataatctaat aaactatagt tcaaaaaaat ttgggttata atagcatata gcccgtgcta    5580
acgtcacgat ctcgcgaacg agggtaaata tgttcacggc ggcggcgcaa gtgagggaag    5640
ggagcagcac tggacaagga cgcaggatta taatttgtag tgataatcta gctagattat    5700
aatctcaaac aaacattcct gattcttgaa tgaaaatgta gcggtagtgc cagtagggtc    5760
atggatctaa atgacgtgat cactgtgatc atatcttgca gctataaata caaaatgcca    5820
atgacaggaa ccagaggagg cacgagagcg ccatacatac acaaacagcg tacaagactc    5880
aaccactccc tccttgtttg tttatatacc ttggcaccac caaggcagca ccctgtaaac    5940
taactaccaa agccgaagaa ggcggcttgc cctgcccgtc gccttggtgc cgcgcgcgcc    6000
atggccaaga gcaagtcgtc cgccaaggcc ggccccccgc tcctcggcaa gtacgagctc    6060
ggccacctcc tcggccgggg caacttcgcc aaggtatacc acgcgcgctg tctcggcgga    6120
ggcgaccccg tggccgtgaa ggtgctggac aaggccgggt tggccgccac gggcatggcg    6180
tcgcgtctcc tgcgcgaggt gtccgccatg cgccgcctga ccacccccaa cgtgctccgc    6240
ctccacgagg tgctggcgac gcgctccaag gtgtacctcg tgatggagct ggccccgggc    6300
ggggacctcc tgacccggct ggcgtcgctg ccgtcgcgca ggctccccga gcacgcggcg    6360
cggcgcgtgt tcctccagct ggcgtcggcg ctcatctaca gccacgcgcg cggggtgttc    6420
caccgcgacg tgaagccgca gaacgtgctg ctggacgccg agggcaacct caaggtgtcc    6480
gacttcggcc tcgcggcgct cccggactcg gtccgcgacg acgggcgcct gcacacggcg    6540
tgcggcaccc cggcgttcgc ggcgcccgag gtgctccggc gcagggccta cgacggcgcc    6600
aaggcggacg cgtggtcctg cggggtcatc ctcttcgtcc tcctcgcggg ccacctcccc    6660
ttcgacgacg ccaacatcgc cgacatgtgc cgcaggcgc accgccggga gtacacggtc    6720
ccgcggtggg tgtcgcagcc ggcgcgccgc ctcgtggcgc gcctgctgga cccgaacccg    6780
```

```
gcgacgcgcc tcgccgtcgc ggagctcgcc ggccacccct ggttcaagcg ctcgctcagc    6840
gtggactccc agctcggcgg cctcctggac ggccaggcgg agcgcgagct ggcgttccag    6900
gccccgccgg cgttgaacgc cttcgacatc atctccatgt cccccgggct ggacctgtcg    6960
ggcctgttcg gcgagggcag gcgccgccgc gagaagcggt catgacgac ggcgtccccg     7020 gagcgggcgg tggagcggct cgcgcaggcc ggcgcgaggc tcggctactt cattgtgggg    7080 aagaagggg ccgagcgcct gccgctgggc gtcctgccgg gcctcgtggc catgtcgatg     7140
gagatgtcgg aggtgtcgcc ggagctgatg ctggtggagc tgaggctgga gggcggccac    7200
ggcgacgagg acgaggcgtt cgggtgggag agctccggg ttgagctggg ggacgtggta     7260
acagcatggc acgtgagtga agaaggttaa aaattcgcaa gaggaaatgc gagaacgatt    7320
tcgcaggtgt atcagtgtag catgtatagc cgtatagcaa gtgcgcatct catctcgtgt    7380
acgtgaaatt agttggttag gacgaacagc agcgtgtgat gttggggatt aactagactg    7440
gtagtttcaa tcaaatgtgt gatgtttggg attatttgtc aaattagtac gtatactaaa    7500
gaccttacta ggtacctcgc gtgattgttg ttcaagtgta ctagctacca agctagtgac    7560
aagaatgttg caaggatata ccagaggaaa ctgtttcaaa gaatgagctt aacttgaact    7620
gattgcagca ttaaaacagt ttccttgtcc agtcgtcgaa tggagctctc caaacttgac    7680
tgcacattcc cattgttgca tggactcgtg gtcttccttc cctgacacg gctgccaaac     7740 cgccgcagcg acgccgtccg aatgatgcag ctagctgcgt gcctgcaccc acccagatcc    7800
agcaaaatac atgctgcctc cgagatcctc ccatgagggc gtggcaaatt ctttcttgtc    7860
tatgtgcttt gggccggggt ggggtggca atgcatctca tctatatgcg gtcaaccgtt    7920
taagtccatc caattaaggt tcaggttcaa ggtgctgtcc aactcgatgt cacctgctcc    7980
ttcatcaggt tgatgaagaa tatatataat accatcccaa ttatggttgg cgaattgaag    8040
aagaaccata gcgcaaaagg ttgacaggca tgtctactag cattacagcg aagattcatg    8100
gtgcaagtcg tagtcggttt acaggcaacg ccctccagca gcaggacta aaatggccat     8160 ggcgtgcgtg atcagatgga tggcgaacgg agaaatttaa aacgagacc acatcatctt     8220 cagtgacttg taggctccgg gctctggcag caccgagctc atggcggacg aggatgaaca    8280
tgtgtcaatg gaactccgtg gaaaccacac accagtcatc ttgctgtcca ttaaacacgt    8340
caaatgtcga cccgcacaag gcacgtacgc gcgcggacca catctctcgt tcatcaagct    8400
agcagcagtt caagtcaact ttgccgaatg catgctaacg gctgaactgt tgattcaagt    8460
agcagtatcg gcaggcagct gcaagctgtg gcctccctgc tacatatact aggtagctag    8520
tggtggtctg gtggatgcgg tgctagatgg ggacgaatga aagcgagaat cagtaagacc    8580
ccggccggag gagaaaaagg agtgatgctc ttggctggca tggacgtcgc cgatcagggg    8640
aaacgaacaa agcgagatcg atcagcccgg caggggtatg gcaagatgac aatgcaagca    8700
gcttgtattg tatccttgtg ccggataatt taattaagca tacagttttc tcccttctga    8760
cgtacggcct catccagcct gcgaagtggt gaaagtgaac tgagcgttac agcagaatac    8820
cagatgcgac tagctgaaac gccgggtttt ggccatagat ccaagagaaa gaagctcaag    8880
tggaaccaca agcgcaagaa actaagaata tattttggtc aggtcatccg tttcacaaga    8940
aaactgagtt tattttcaat tcagatgcat catgataata ggcagcagac cagaaggcaa    9000
aaaaaaaaaa aaaaaaaaag agttcttcat cgctttgatc tgaccatcta tctcttcaac    9060
catggcccat ggggcaatcc taactggaac ccagaaataa gccgcccct tccttaagct     9120
```

-continued

```
agacagaaga agacgcccat tatagtgtct aataacggtg ttaattaagt tgagtagtag    9180
catgcatgaa tactatcggg aagaatatgt cagatattgc tgaaagcatg taattaagtt    9240
gagtagcggc atgcatgaat ctagggccag caagtctgac ccggacgggc ggaccggaga    9300
gggctctccc tctccaacag tccaactact accgcaactg tcaacgcaag cataggcat     9360
ccaaaactga agatgaacga tacctaacac cccctgcatt agtgcacaac ttcgttgtcg    9420
tcttgctgcc gtcatgtact cgattagtct aattgtgtct agccattgga cgtgaagaaa    9480
aaggttctcc tccttccctt gtgccaaaat aaataaataa acgaagggca aagggcaaga    9540
tcaagcgagt ggtcacgatc agaggtgtac agtacagttg tacatgcatg tttctggaat    9600
ctgatcagtg gactcggagt gcgaatcaat cagtcaaggt gctaaaaaga agctacaaat    9660
gtgcacgctt cttcatcttg tgcatcccat tctgtgtgag aaagagagag agagagagag    9720
agagagagag agagagagag agagagagag agagagagag agagagagag agagaggtga    9780
atggcacact tctagcaagt tcttgtagca cggacaacga aagggtgagc tttgaaaagt    9840
acactccacg aaggatatgc aaaaaaatga ataggcccg aaagttcaat tagacagtcc     9900
aattccgaag cacccacaaa ttggttgttg gcccatgaag cacccacaac accctgtatc    9960
tcgtccagcc cactttgcat ccaatccaac ggcaacgggc aacgaaatgg caccgtgtta    10020
cacgaacacg cgtcacacga cgggaatgtc agaagtcaga acagctcgtt cgtccgtcac    10080
caactcgcca tagatgatag aacgctatcc catcttcaca cacaaaaata tccgcgcgac    10140
cccgacctcc cccctcccac tccgggcagc agccagcagc cagcaggcat ggggataccc    10200
gtggtggttc ccgtcgcggc ggcctactcg tgctcctcct ccctcgccgc gccaccgagg    10260
gccgccgccg ccgcggcgag ggcgccgagc cgcgcgcacg tcgcggcggc cgggatgtcc    10320
tccagggcgt cctccttcgt cggggcagc ggaggcgacc tcgcggcggt ggccgcgtcg     10380
gtagccgcgc ggcccaggag ggcgggctcc gggggaggcg gcgcgctcgg gtgcaagtgc    10440
ctcttcgggc tcggcgtgcc ggagctcgcc gtcatcgccg gcgtcgccgc gctcgtgttc    10500
gggcccaagc agctccccga gatcggccgc agcatcggca agaccgtcaa gagcttccag    10560
caggtgaggg ttggggcatg aatccaaatg gcgtggtcag tagaagctcg cggttgctgg    10620
gggggcgatg ctgacaatcg tttgactgct agttagcagc tgcggaaact tgtcaccccg    10680
ttttgctcga gatgctaaag cttaggtctt cttcgtagtg ttaccaatct gcaagtcatt    10740
gctttggtag ctatgaatat gcaggcggag gaagtatcct caccccccaca ccccggcgc    10800
gctgaaccgt ataaaaaaag tttggctgat ttcggtactc tagtagataa tattgttcag    10860
tttggcagct aatacagtgg cccagtaaat cacattcatt gcaaatttgc attttggctc    10920
ggctgtgctg ttgaccgctt agtgggatgc caatggtagg atatatgcc acattgcttc     10980
ctcattttga cttatgagca gtgttcttaa ggcgcctagg cgagcaagca aacactccga    11040
gcgccttagc gcctacgcgg gcaaggcggc aaggtttagc cgagcgcccg cctaggcgac    11100
gccttaaaaa ccctgcttat gagttatgtt tttttatatg ccagtgtgat gagtggtgtg    11160
ggtacaggga tgtaagattg gagtgataga aatttctgca cctcattctt tctgaactgc    11220
aatgggaagt agtagaacat atcttccaat ttagtactac ctcttgtcgg atttaggtga    11280
cgttttggaa aatcaaaaag attggagcaa gtagttgttt gagatggagc caaaatttgg    11340
tgtggtttgt tcttgcccat ttggagttgt ataatctctt aagagtcctg catgttatga    11400
tatgtcagg gttttttttg gtcgccgatg aattatgtca tatacaagct aggcctgtag     11460
ctgtagcaaa gataacagtt gttacccttta gggcctattt ggaagctctg taatttccta   11520
```

-continued

```
gtttcaaggt aatactgtag tattggagaa taccatagtt ttataggcta aaaggtgttt    11580
ggttggtcct ttcaaaactc tgttttcaat actatggttt gtcaatacta tagaattttt    11640
gtggtgttgg atacttcaat cttgacccaa gttttctttg cgcaagagca gctcgcagca    11700
cacagaataa tggaaacaaa cacacttcgg tttcaaaaaa ataccatggt ttaaatagag    11760
taatcgaaac tacagtattc atgtcacaac caaaaaaatg ctattgtatt ctaaaaccac    11820
agtattagaa aacaatgctg ccaaacaggc cttacgtgtt agagtgttac ctattgagat    11880
tcagctgact ttacatttat tataaaatga taaccccacg atgctaaatt ttcattgctt    11940
ttaaaatcaa gaagggggta attgtcttga gaatagtccc acattgtgtg ttgtggagaa    12000
gcaatcatgg tttatatgtt tgagggtgca agtgcaaccc cctaatgggc aagccttttg    12060
gggggagtat tggcccaaca gacctaaagc ccgctgctat gcgtgcgtgc gcgtgtgtcg    12120
cggcccgatg acttggatag gcgcgccgtg tggtgggtgg cccgacggac acgccatgtg    12180
ttggtggttc agtttaggtc cggttccaac aattggtatc aaagccagat tgacccagtg    12240
tattctcaga caaatctcgg ctcacaatgt gtgagggaga gattgttgag aatagtccca    12300
catagtgggt gcaccccct aatgggttag cttttttgga gagtattggc ccaacagacc    12360
taaatctcgc tgtcatgtgt gcggacgcgt gtgtcgcggc ctgacagcct tggtaggcgc    12420
gctgtatgtg cggatacgcc atgtgtcggc ggtccggttc caacaaattg gtctaaaact    12480
gaggccattt gtggtttatg atctatgttt tggtcgttgc caacttacat gctgatatgg    12540
cttacccaat tctacttgat aggagataaa gctgcagaga agaaatggtt taaaggtggc    12600
gtgtaaaagt tgaaaagtgt ttccatttta gtccaacttg ttttaggagg cagggtgtgc    12660
ggaaattagt gtctagagac tagagatatg tcacccacag gccacagggc cacattacca    12720
ctagtttgat aatttcatca ttacttagaa gaatgatatg cctgcttcct tttggtctca    12780
cttgtctaag aatttgatgg gactgatcca ccttagcctg caccattata ctaattgaaa    12840
gcttgttgag ttgcatacac ttcgtgctct gtttctgaag atcaagtttt ctgaccagca    12900
ttatttcctt ttccattcag taaaattgtt ccgtgatcca tccaacttct ctcgcaggcg    12960
gctaaggagt ttgaaactga actgaagaaa gagcctgggg aaggcggcga tcagccccca    13020
cctgcaactc ccacagctgt aagtggcggg gaggagaagg ggcttgaggc atctagtagc    13080
aaggagagcg cgtgaggatc aggatctatc tagtgttgtt tatgaaaatt gtattctggg    13140
cttctcgagt tagcagttca tatccttta accgcatcgc ggtttcaggc catgtagcga    13200
tattgtttgt agtttgtacc gggaataaca tatttggttg agcttctacg tattgaagaa    13260
acaacttatc tgtgaagctg acgcgaacaa                                    13290
```

```
<210> SEQ ID NO 3
<211> LENGTH: 32
<212> TYPE: DNA
<213> ORGANISM: Artificial Sequence
<220> FEATURE:
<223> OTHER INFORMATION: synthetic

<400> SEQUENCE: 3
agagaagcca acgccawcgc ctcyatttcg tc                                  32

<210> SEQ ID NO 4
<211> LENGTH: 26
<212> TYPE: DNA
<213> ORGANISM: Artificial Sequence
<220> FEATURE:
```

```
<223> OTHER INFORMATION: synthetic

<400> SEQUENCE: 4
ttggcaccac caaggcgcac cctgta                                              26

<210> SEQ ID NO 5
<211> LENGTH: 21
<212> TYPE: DNA
<213> ORGANISM: Artificial Sequence
<220> FEATURE:
<223> OTHER INFORMATION: synthetic

<400> SEQUENCE: 5
cgtccgcctt ggcgccgtcg t                                                   21
```